US012635746B2

(12) United States Patent
Chandler et al.

(10) Patent No.: US 12,635,746 B2
(45) Date of Patent: **\*May 26, 2026**

(54) PROTECTIVE MASK

(71) Applicant: INTELLISAFE LLC, Denver, CO (US)

(72) Inventors: Trevor Chandler, Thornton, CO (US); Michael Brown, Golden, CO (US); Joshua Eng-Morris, Denver, CO (US); Joshua K. Goetz, Denver, CO (US)

(73) Assignee: INTELLISAFE LLC, Denver, CO (US)

( \* ) Notice: Subject to any disclaimer, the term of this patent is extended or adjusted under 35 U.S.C. 154(b) by 861 days.

This patent is subject to a terminal disclaimer.

(21) Appl. No.: 17/839,242

(22) Filed: Jun. 13, 2022

(65) Prior Publication Data

US 2022/0304404 A1     Sep. 29, 2022

Related U.S. Application Data

(63) Continuation of application No. 17/362,619, filed on Jun. 29, 2021, now Pat. No. 11,382,370.

(60) Provisional application No. 63/177,321, filed on Apr. 20, 2021, provisional application No. 63/066,582, (Continued)

(51) Int. Cl.
A41D 13/11     (2006.01)
A61L 9/20     (2006.01)

(52) U.S. Cl.
CPC ............ A41D 13/1161 (2013.01); A61L 9/20 (2013.01); A41D 2300/33 (2013.01); A61L

2209/12 (2013.01); *A61L 2209/133* (2013.01); *A61L 2209/14* (2013.01)

(58) Field of Classification Search
None
See application file for complete search history.

(56) References Cited

U.S. PATENT DOCUMENTS

| | | | |
|---|---|---|---|
| 3,878,563 A | 4/1975 | Pulju | |
| 3,991,753 A | 11/1976 | Mesca | |
| 4,694,179 A | 9/1987 | Lew et al. | |

(Continued)

FOREIGN PATENT DOCUMENTS

| | | | |
|---|---|---|---|
| CA | 486317 A | 9/1952 | |
| CN | 2616236 Y | 5/2004 | |

(Continued)

OTHER PUBLICATIONS

Shiu, J. TW592747B-translsted document (Year: 2004).*

(Continued)

*Primary Examiner* — Jelitza M Perez
(74) *Attorney, Agent, or Firm* — Dorsey & Whitney LLP

(57)          ABSTRACT

A protective mask includes a transparent impermeable membrane; a frame that substantially surrounds and is coupled to a perimeter of the impermeable membrane and is configured to be positioned about a face of a user; a seal operatively coupled to the frame that seals against a face of the user and extends around a perimeter of the frame, wherein the frame and the seal are substantially impermeable to the passage of air therethrough; an air passageway formed in the frame; and a filter element disposed to filter air passing through the air passageway. The air passageway and the filter element are disposed on a bottom portion of the frame.

18 Claims, 38 Drawing Sheets

Related U.S. Application Data filed on Aug. 17, 2020, provisional application No. 63/045,749, filed on Jun. 29, 2020.

(56) References Cited

U.S. PATENT DOCUMENTS

| | | | |
|---|---|---|---|
| 4,764,990 | A | 8/1988 | Markert |
| 4,796,621 | A | 1/1989 | Barle et al. |
| 5,088,114 | A | 2/1992 | Salce et al. |
| 5,165,395 | A | 11/1992 | Ricci |
| D374,951 | S | 10/1996 | Machson |
| 6,233,748 | B1 | 5/2001 | Gieger et al. |
| 7,178,931 | B1 * | 2/2007 | Murphy ................. A62B 18/08 |
| | | | 362/105 |
| D568,545 | S | 5/2008 | Schaffner |
| D640,011 | S | 6/2011 | Teng |
| 8,567,403 | B1 | 10/2013 | Lu et al. |
| 10,335,618 | B2 | 7/2019 | Zhou et al. |
| 10,449,397 | B2 | 10/2019 | Vanderwoude et al. |
| D907,226 | S | 1/2021 | Park et al. |
| D930,254 | S | 9/2021 | Hong et al. |
| D941,480 | S | 1/2022 | Kim |
| D945,078 | S | 3/2022 | Wu et al. |
| D949,357 | S | 4/2022 | Yao |
| D949,485 | S | 4/2022 | Wu et al. |
| D957,661 | S | 7/2022 | Kwon et al. |
| 11,382,370 | B2 | 7/2022 | Chandler et al. |
| D959,754 | S | 8/2022 | Hughes |
| D973,863 | S | 12/2022 | Chandler |
| 2003/0111075 | A1 | 6/2003 | Wen |
| 2007/0163588 | A1 | 7/2007 | Hebrank et al. |
| 2008/0083411 | A1 | 4/2008 | Guth |
| 2009/0004047 | A1 | 1/2009 | Hunter et al. |
| 2009/0014002 | A1 | 1/2009 | Krafthefer et al. |
| 2010/0132715 | A1 | 6/2010 | Litz |
| 2010/0229275 | A1 | 9/2010 | Wilson |
| 2013/0180529 | A1 | 7/2013 | Matich |
| 2015/0114397 | A1 | 4/2015 | Litz |
| 2015/0237931 | A1 | 8/2015 | Miller et al. |
| 2016/0001108 | A1 | 1/2016 | Zhou et al. |
| 2016/0030779 | A1 * | 2/2016 | Twu ....................... A62B 18/02 |
| | | | 128/202.13 |
| 2016/0038624 | A1 | 2/2016 | Krosney |
| 2018/0311515 | A1 | 11/2018 | Wilson et al. |
| 2021/0330853 | A1 | 10/2021 | Mizandari |
| 2021/0401084 | A1 | 12/2021 | Lamoncha |
| 2021/0401086 | A1 | 12/2021 | Chandler et al. |

FOREIGN PATENT DOCUMENTS

| | | | | |
|---|---|---|---|---|
| CN | 2631539 | Y | | 8/2004 |
| CN | 101213007 | A | | 7/2008 |
| CN | 101579152 | A | * | 11/2009 |
| CN | 101678139 | A | | 3/2010 |
| CN | 102871240 | A | | 1/2013 |
| CN | 111053984 | A | | 4/2020 |
| CN | 111150152 | A | | 5/2020 |
| CN | 111165940 | A | | 5/2020 |
| CN | 111938231 | A | | 11/2020 |
| JP | 2005512641 | A | | 5/2005 |
| KR | 20080113383 | A | | 12/2008 |
| KR | 20190138151 | A | | 12/2019 |
| KR | 20200020747 | A | | 2/2020 |
| TW | 592747 | B | * | 6/2004 |
| WO | 03051460 | A1 | | 6/2003 |

OTHER PUBLICATIONS

Miu, J. CN101579152A-translated document (Year: 2009).*

European Patent Office, "Extended European Search Report," mailed Jul. 8, 2024, for European Application No. 21834325.9, 10 pages.

National Intellectual Property Administration, P.R. China, "English Translation of First Office Action and Search Report," mailed Jul. 20, 2023, for Chinese Application No. 202180053690.5, 15 pages.

Japanese Patent Office, "Non-Final Office Action," mailed Jul. 7, 2023, for Japanese Patent Application No. 2023-524486, with English Translation, 9 pages.

Korean Patent Office, "Notice of Preliminary Rejection," mailed Jun. 5, 2023, for Korean Patent Application No. 10-2023-7002785, with English Translation, 19 pages.

"PCT International Search Report and Written Opinion", mailed Oct. 13, 2021, for PCT Application No. PCT/US2021/039588, 13 pages.

Twice.com, CRL Public Relations , "Oracle Lighting Develops COVID-19/Virus Neutralizing UV-Light Face Mask for Consumer/ Medical Use", Jun. 15, 2020, website: https://www.twice.com/the-wire/oracle-lighting-develops-covid-19-virus-neutralizing-uv-light-face-mask-for-consumer-medical-use, 8 pages.

Electro Optics—Photonics business, applications & technology, "Covid-19: Photonics unravelling virus conundrum," May 2020, Issue 303, 48 pages.

Indiegogo, "Leaf Mask, World's first FDA, UV-C N99, Clear mask," Jul. 30, 2020, website: https://www.indiegogo.com/projects/leaf-mask-world-s-first-fda-uv-c-n99-clear-mask#/, 57 pages.

Kickstarter, "UV Mask: Real-Time UV-C Filtration & Purification Face Mask," UM Systems, Jul. 20, 2020, website: https://www.kickstarter.com/projects/umsystems/uvmask-inactivate-9999-of-all-pathogens-and-air-pollutants, 61 pages.

Sonovia, "Masks: Protect Your Loved Ones: Buy an antiviral masks [sic] that will help you and your loved ones stay safe from harmful bacteria and viruses," Accessed Jul. 2, 2020, website: https://sonoviatech.com/shop/, 7 pages.

Indian Patent Office, "Examination Report," mailed Sep. 10, 2025, for Indian Application No. 202317001698, 9 pages.

* cited by examiner

600

600

600

700

700

700

700

PROTECTIVE MASK

CROSS-REFERENCE TO RELATED APPLICATIONS

This application claims the benefit of priority pursuant to 35 U.S.C. § 120 of U.S. patent application Ser. No. 17/362,619, titled "Protective Mask" filed Jun. 29, 2021 which claims the benefit of priority pursuant to 35 U.S.C. § 119(e) of U.S. provisional patent application No. 63/045,749, titled "Protective Mask" filed Jun. 29, 2020; U.S. provisional patent application No. 63/066,582, titled "Protective Mask" filed on Aug. 17, 2020; and U.S. provisional patent application No. 63/177,321, titled "Protective Mask" filed on Apr. 20, 2021, titled "Protective Mask"; and is related to U.S. design Patent Application Ser. No. 29/739,808, titled "Mask" filed Jun. 29, 2020; and is related to the U.S. design Patent Application Ser. No. 29/797,193, titled "Mask" filed Jun. 29, 2021 all of which are hereby incorporated by reference herein in their entireties.

BACKGROUND

As the spread of viruses, bacteria, and other contaminants becomes a cause of global concern, people have sought to limit the spread of such viruses and disease through the use of face coverings. Face coverings may limit the passage of droplets such as saliva, sputum, mucus, or other bodily excretions that may contain damaging agents such as damaging agents like viruses, bacteria, mold spores, or the like. Some face coverings may limit a user's ability to inhale such droplets and/or limit a user's ability to exhale or excrete such droplets, thereby protecting others from infection by the user. Traditionally, face coverings may be made from a woven fabric, non-woven material, foam, or other material that can capture droplets as a user inhales or exhales. Such materials may not be effective at trapping small droplets and may allow damaging agents, especially viruses, to pass through. Additionally, traditional face coverings may be difficult to clean and may become permeated with damaging agents that cannot readily be removed or neutralized. These materials also may present a security risk, as they are typically opaque, covering a user's face so the user may not be readily identified.

SUMMARY

In one embodiment, a protective mask is disclosed. The mask includes a permeable membrane including a nose and mouth cover portion and a filter cartridge removably attachable to the impermeable membrane. The filter cartridge may include a housing that supports a filter element operative to trap particles of a damaging agent, a sanitizing emitter surrounding an exterior perimeter of the filter element and acting to permeate the filter element with a sanitizing agent operative to deactivate the particles of the damaging agent, and a containment element that contains the sanitizing agent. In one embodiment, the containment element protects the user from exposure to the sanitizing agent.

Optionally, in some embodiments sanitizing agent source electrically coupled to the sanitizing emitter.

Optionally, in some embodiments the sanitizing emitter comprises a light source; the sanitizing agent comprises light; and the sanitizing agent source comprises a power supply.

Optionally, in some embodiments, the light source is a plurality of light emitting diodes.

Optionally, in some embodiments, the light comprises light in an ultraviolet spectrum.

Optionally, in some embodiments, the light comprises a wavelength of about 220-280 nanometers.

Optionally, in some embodiments, the power supply is rechargeable.

Optionally, in some embodiments, the power supply comprises a battery disposed within the housing.

Optionally, in some embodiments, the filter cartridge is a first filter cartridge, the protective mask further comprising a second filter cartridge stacked in series with the first filter cartridge.

Optionally, in some embodiments, the first filter cartridge is configured to deactivate a first type of damaging agent, and the second filter cartridge is configured to deactivate a second type of damaging agent.

Optionally, in some embodiments, the filter element filters particles above about 50 microns in size.

Optionally, in some embodiments, the protective mask includes a transparent eye cover portion. The transparent eye cover portion and the nose and mouth cover portion are unitarily formed with the impermeable membrane.

Optionally, in some embodiments, the mask includes an attachment member configured to hold the impermeable membrane to a face of the user and a sealing element configured to seal the impermeable membrane to the face of the user when held thereto by the attachment member. The sealing element includes a first seal and a second seal disposed inward from an edge of the impermeable membrane with respect to the first seal.

Optionally, in some embodiments, the containment element is a first containment element disposed transversely outward from the sanitizing emitter such that the first containment element surrounds an exterior perimeter of the sanitizing emitter and contains the sanitizing agent in a transverse direction. In some embodiments, the protective mask includes a second containment element disposed longitudinally relative to the filter element that contains the sanitizing agent in a longitudinal direction.

Optionally, in some embodiments, the sanitizing emitter is directly adjacent to the exterior perimeter of the filter element.

Optionally, in some embodiments, the sanitizing emitter includes a plurality of emitting elements disposed uniformly from a center of the filter element.

Optionally, in some embodiments, the filter element has a circular cross section.

Optionally, in some embodiments, the sanitizing mask includes a channel formed between the first seal and the second seal and an air mover disposed within the channel. The first and second seals and air mover form a closed loop cooling area configured to cool a face of a user while wearing the protective mask.

Optionally, in some embodiments, the containment element forms a tortuous path configured to allow air to pass through the containment element and configured to block the sanitizing agent emitted by the sanitizing emitter from passing through the containment element.

Optionally, in some embodiments, wherein the filter cartridge includes a reflective chamber configured to reflect the sanitizing agent.

In one embodiment, a protective mask includes a transparent impermeable membrane including a nose cover portion, a mouth cover portion, and a chin cover portion. A face of a user is visible through the transparent impermeable membrane while the user is wearing the protective mask. A filter cartridge is removably attachable to the transparent impermeable membrane in the chin cover portion including a housing that supports a filter element operative to trap particles of a damaging agent, sanitizing emitter surrounding an exterior perimeter of the filter element and acting to permeate the filter element with a sanitizing agent operative to deactivate the particles of the damaging agent, and a containment element that protects the user from exposure to the sanitizing agent.

In one embodiment a facial mask includes a lens; a frame coupled to the lens that extends around a perimeter of the lens; and a filter cartridge coupled to the frame. The filter cartridge filters an air flow into and out of the facial mask.

Optionally, in some embodiments, the lens is configured to cover a nose, eyes, and a mouth of a wearer of the facial mask.

Optionally, in some embodiments, a seal coupled to the frame and extending around the perimeter of the lens.

Optionally, in some embodiments, the filter cartridge is configured to be manipulated to replace a filter positioned therein.

Optionally, in some embodiments, the filter cartridge is removable from the frame.

Optionally, in some embodiments, the filter cartridge is positioned on a bottom edge of the frame.

Optionally, in some embodiments, the lens comprises an anti-fog treatment that resists fogging of the lens during use.

Optionally, in some embodiments, the frame and the seal are formed of transparent or substantially transparent materials.

In one embodiment a protective mask includes a frame including a first frame portion and a second frame portion coupled to one another at a joint. The frame extends around a perimeter of a face of a user wearing the protective mask. The protective mask includes a transparent impermeable membrane coupled to the frame and including a first portion, where the face of the user is visible through the transparent impermeable membrane while the user is wearing the protective mask. The mask includes a cartridge receptacle including a containment element coupled to the frame. A filter cartridge is removably attachable to the cartridge receptacle and includes housing that supports a filter element operative to trap a damaging agent, and a sanitizing emitter and acting to permeate the filter element with a sanitizing agent operative to deactivate the damaging agent, wherein the containment element protects the user from exposure to the sanitizing agent.

Optionally, in some embodiments, the protective mask includes a battery compartment coupled to the first frame portion and operative to receive at least one battery, the at least one battery in electrical communication with the sanitizing emitter and operative to provide electrical power to the sanitizing emitter.

Optionally, in some embodiments, the sanitizing emitter comprises: a circuit board operative to distribute the electrical power from the at least one battery to at least one emitting element such that the at least one emitting element emits the sanitizing agent.

Optionally, in some embodiments, the circuit board comprises a flexible circuit board that bends to conform to the shape of the housing.

Optionally, in some embodiments, the protective mask includes a first gasket including a plurality of apertures formed in a body thereof. The first gasket is received in the housing, and the sanitizing emitter is disposed on the first gasket.

Optionally, in some embodiments, the plurality of apertures forms a plurality of ribs operative to support the sanitizing emitter.

Optionally, in some embodiments, the protective mask includes a second gasket including at least one aperture formed in a body thereof. The second gasket is received in the housing, and the filter element is disposed on the second gasket.

Optionally, in some embodiments, the first gasket and the second gasket seal at least one of the housing or the cartridge receptacle so as to reduce or prevent a bypass of air or the damaging agent around the sanitizing emitter or the filter element.

Optionally, in some embodiments, the protective mask includes a controller received in the cartridge receptacle. The controller is in electrical communication with the at least one battery and the sanitizing emitter and is operative to control the sanitizing emitter.

Optionally, in some embodiments, the controller includes at least one indicator operative to indicate a status of the protective mask.

Optionally, in some embodiments, the controller includes a power actuator operative to control power supplied from the at least one battery to the sanitizing emitter.

Optionally, in some embodiments, controller includes a reset actuator operative to reset an operation of the protective mask.

Optionally, in some embodiments, the protective mask includes a sanitizing agent source electrically coupled to the sanitizing emitter.

In some embodiments, a protective mask includes a transparent impermeable membrane; a frame that substantially surrounds and is coupled to a perimeter of the impermeable membrane and is configured to be positioned about a face of a user; a seal operatively coupled to the frame that seals against a face of the user and extends around a perimeter of the frame, wherein the frame and the seal are substantially impermeable to the passage of air therethrough; an air passageway formed in the frame; and a filter element disposed to filter air passing through the air passageway. The air passageway and the filter element are disposed on a bottom portion of the frame.

Optionally in some embodiments, the protective mask includes a pocket defined in the frame and configured to receive the filter element, wherein the pocket is positioned such that eyes, a nose, and a mouth of the user are not obscured by the cartridge and the frame.

Optionally in some embodiments, the seal includes a bottom extension portion that extends inward toward the interior surface of the impermeable membrane and defines an extended surface area for the seal.

Optionally in some embodiments, the bottom extension is configured to seal against a chin of the user to maintain a seal as the user moves his mouth.

Optionally in some embodiments, the pocket is defined on a bottom edge of the frame.

Optionally in some embodiments, the protective mask includes: a cartridge body coupled to the filter element, the cartridge body is disposed in the air passageway; and the cartridge body includes a lip that extends upward from a top surface of the cartridge body.

Optionally in some embodiments, the filter element is positioned within the pocket and expands against an interior surface of the lip.

Optionally in some embodiments, the filter element is configured to substantially fill the pocket, such that substantially any air flow through the cartridge body is through the filter element.

Optionally in some embodiments, the filter element is larger than the pocket in an uncompressed state and compressible to a second state wherein the filter element is positionable in the cartridge body via friction fit.

Optionally in some embodiments, the cartridge body is selectively removable from the pocket.

Optionally in some embodiments, the protective mask includes an illumination emitter configured to generate light that permeates the filter element from the exterior perimeter thereof.

In some embodiments, a protective mask include a transparent impermeable membrane including a first portion configured to extend substantially from a forehead of a user to a chin of the user; a frame coupled to a perimeter of the impermeable membrane; and a seal operatively coupled to the frame that seals against a face of the user and extends around a perimeter of the frame an air passageway formed in the frame; and a filter element disposed to filter air passing through the air passageway, wherein the air passageway and the filter element are disposed on a bottom portion of the frame.

Optionally in some embodiments, the impermeable membrane further includes two second portions disposed on respective left and right sides of the first portion; the impermeable membrane comprises a third portion configured to extend across the chin of the user between the two second portions; and an inflection between the first portion and the third portion is positioned below a mouth of the user.

Optionally in some embodiments, the cartridge receptacle coupled to a lower portion of the frame and configured to receive a filter assembly, the filter assembly comprising a first circuit board including one or more sanitizing emitters.

Optionally in some embodiments, the protective mask includes a first gasket including a plurality of first apertures formed therein.

Optionally in some embodiments, the protective mask includes a filter element configured to trap particles of a damaging agent; and a second gasket including a second aperture, wherein the first circuit board, the first gasket, the filter element, and the second gasket are arranged in a stacked configuration.

Optionally in some embodiments, the one or more sanitizing emitters is positioned so as to illuminate an exterior perimeter of the filter element and acting to permeate the filter element from the exterior perimeter with a sanitizing agent operative to deactivate the particles of the damaging agent.

Optionally in some embodiments, the protective mask includes a second circuit board configured to control an aspect of the protective mask, wherein the second circuit board is disposed in within a volume defined by the frame.

Optionally in some embodiments, the aspect of the protective mask includes at least one of the first circuit board or the one or more sanitizing emitters.

Optionally in some embodiments, the filter element and the air passageway are configured to be positioned adjacent to or beneath a chin of a user.

In some embodiments, a method of protecting a user from a damaging agent includes: trapping the damaging agent in a filter element; permeating the filter element from the exterior perimeter thereof with a sanitizing agent; deactivating the particles of the damaging agent with the sanitizing agent.

7

Figure 19A:
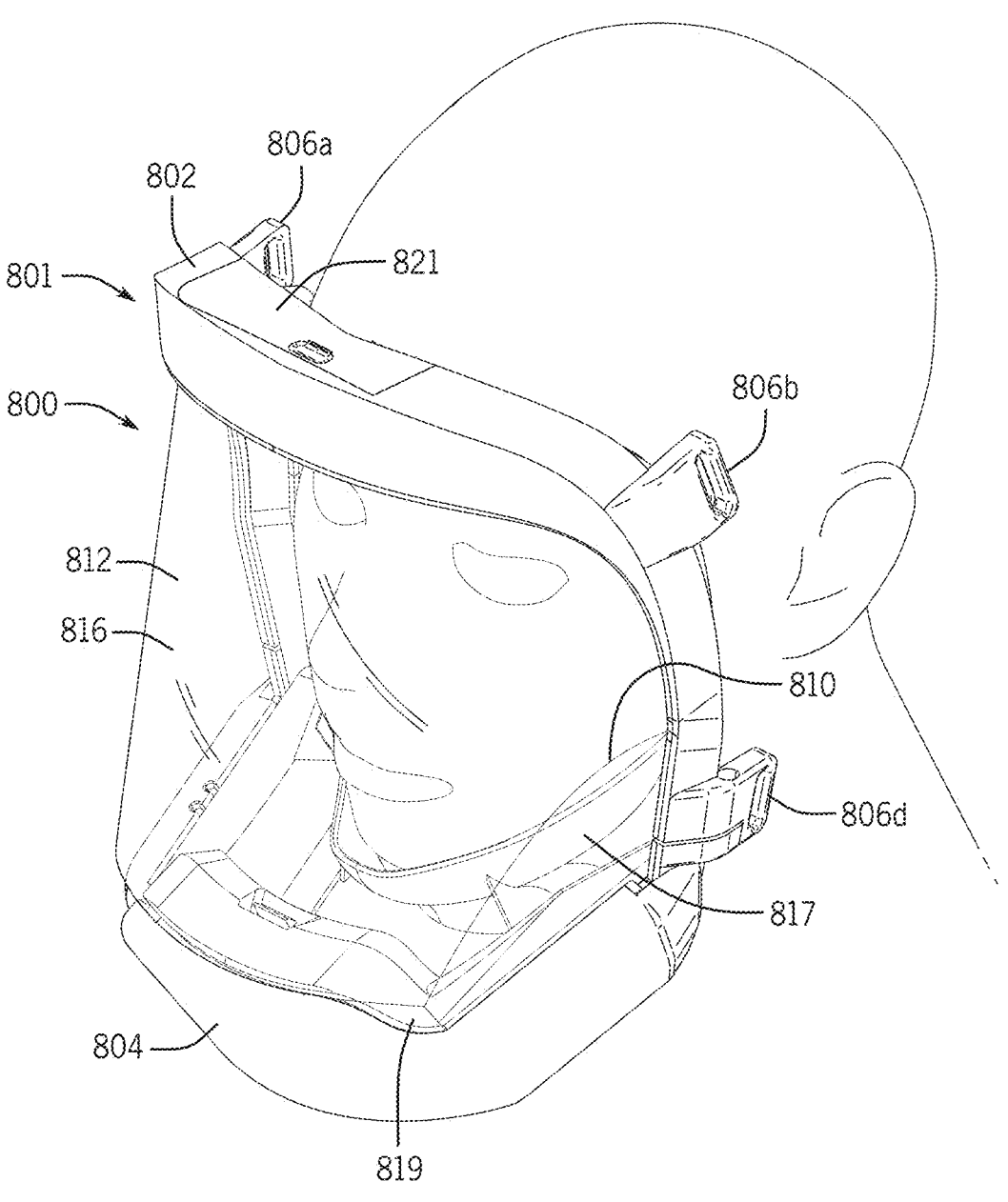
FIG. 19A is a front isometric view of a mask as worn by a user.
Figure 19B:
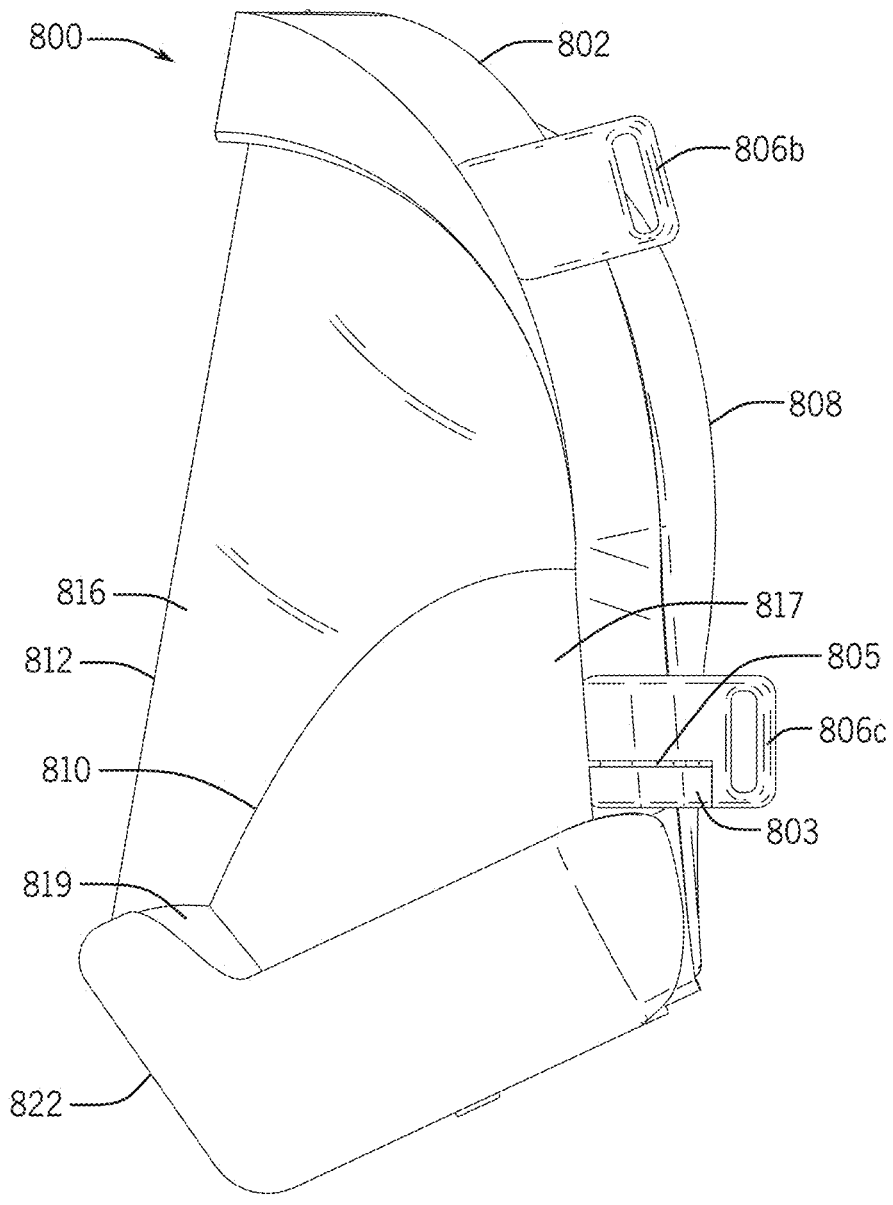
FIG. 19B is a side elevation view of the mask of FIG. 19A.
Figure 19C:
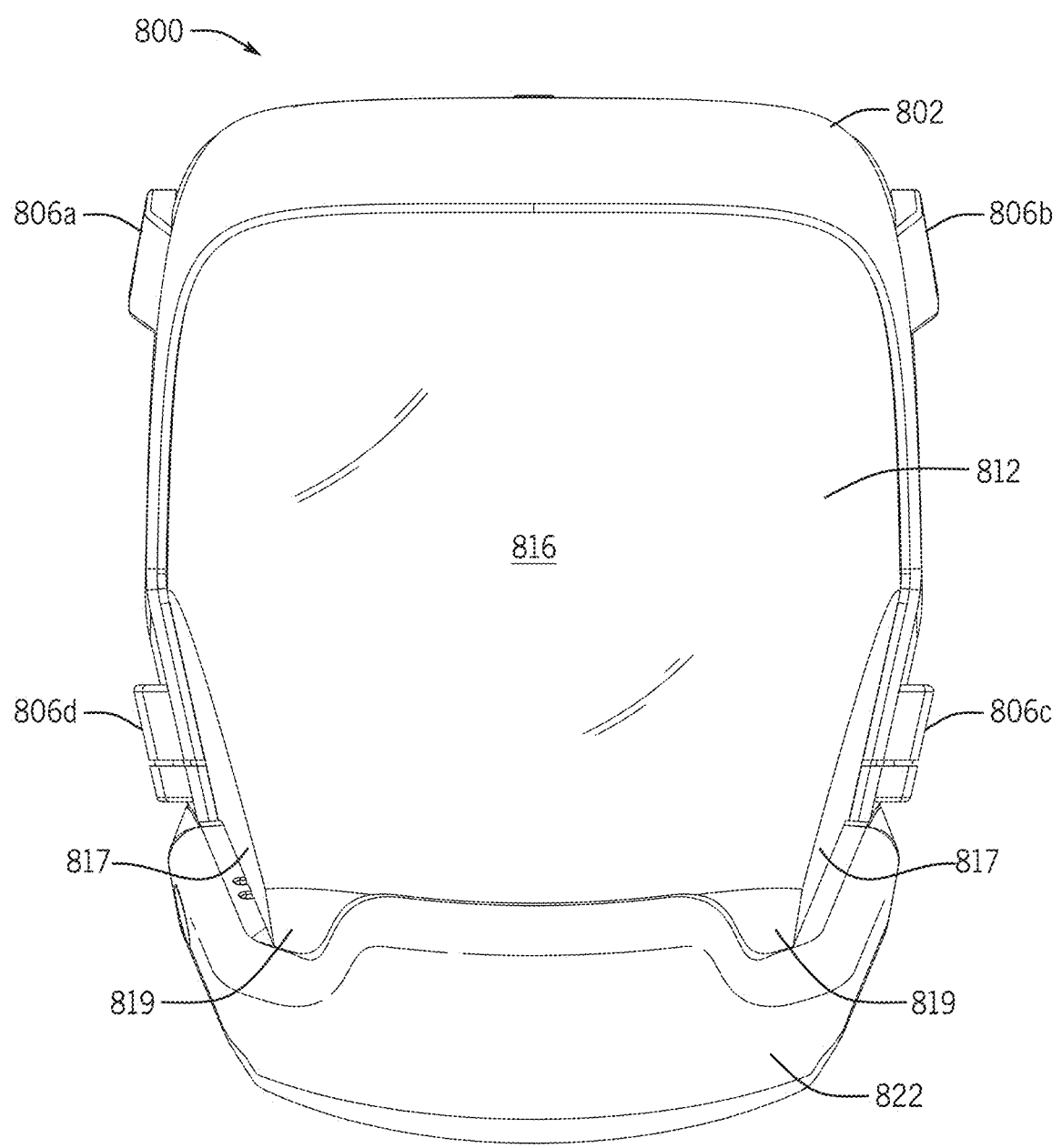
FIG. 19C is a front elevation view of the mask of FIG. 19A.
Figure 19D:
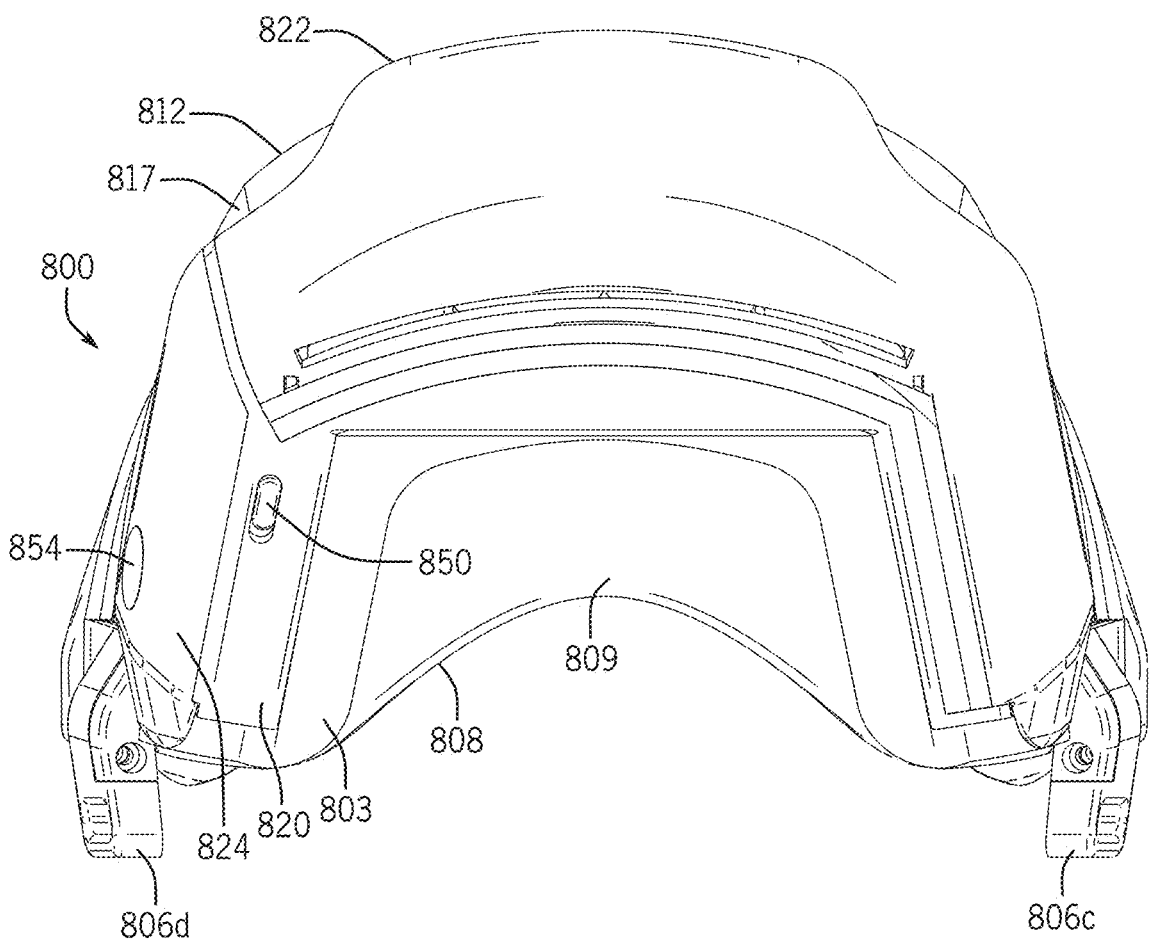
FIG. 19D is a bottom plan view of the mask of FIG. 19A.
Figure 19E:
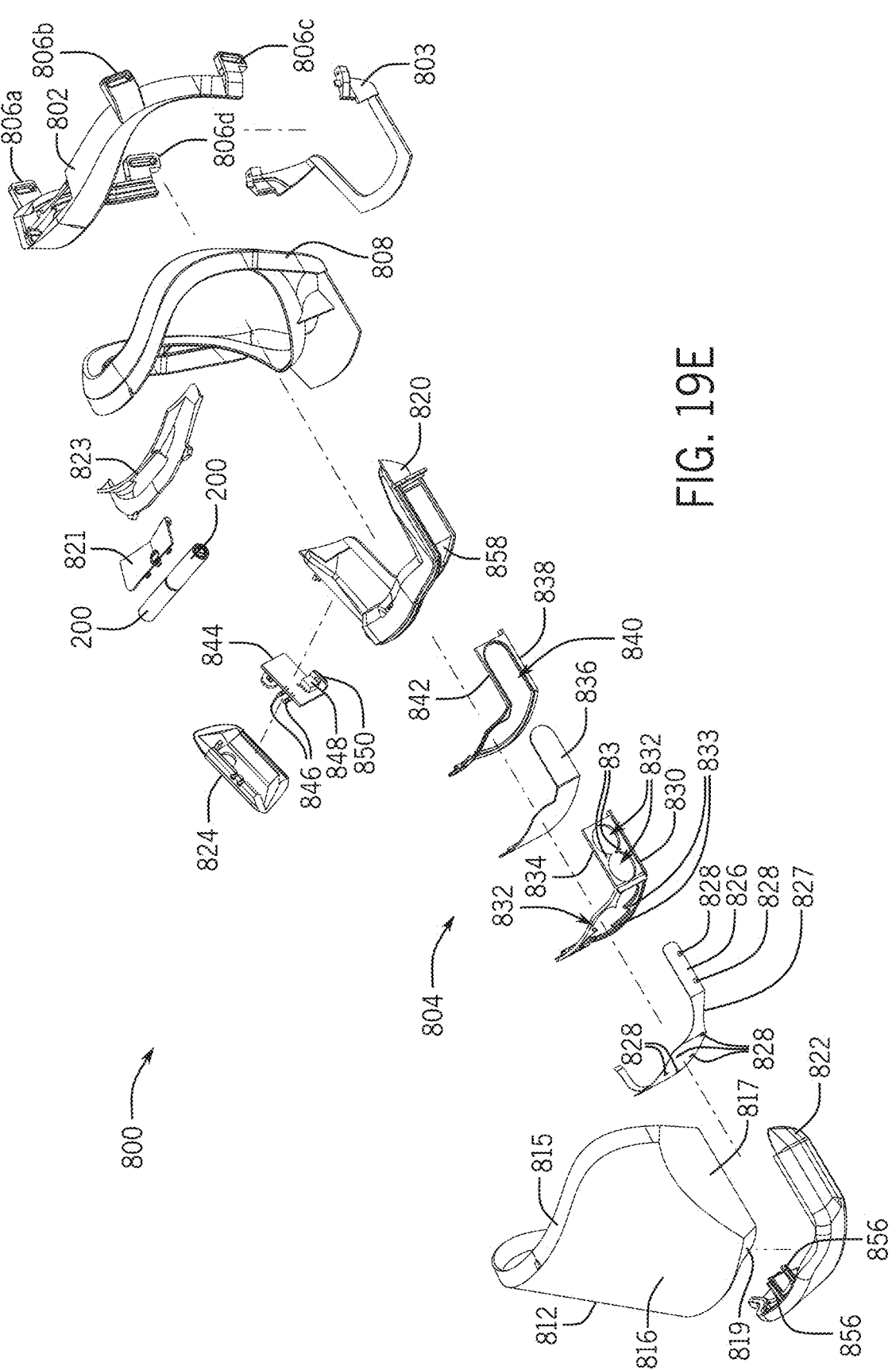
FIG. 19E is an exploded isometric view of the mask of FIG. 19A.
Figure 19F:
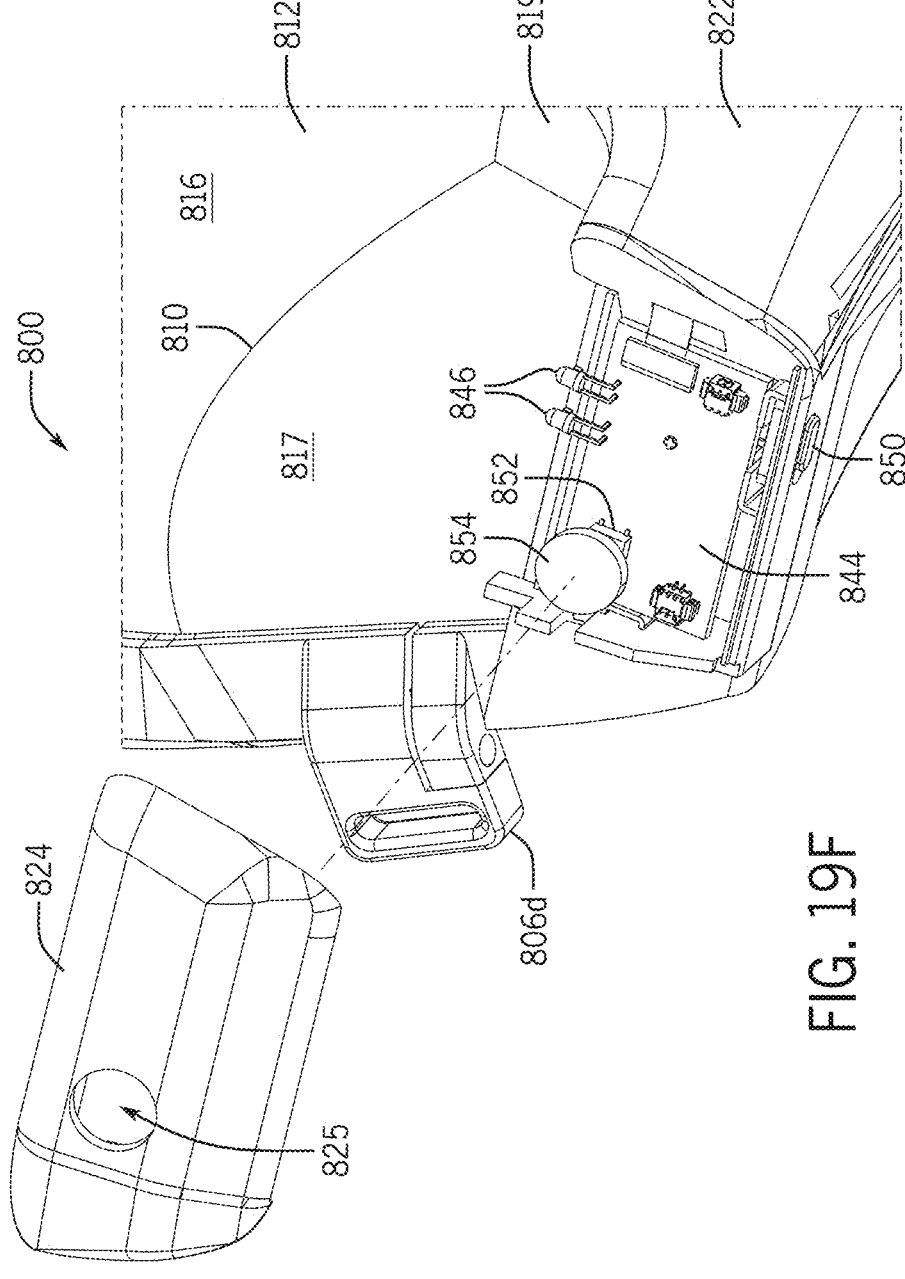

FIG. 19F is a partial isometric detail view of a portion of the mask of FIG. 19A.

DETAILED DESCRIPTION

The present disclosure relates to protective masks that help to prevent contamination from damaging agents. As used herein, "damaging agent" refers to any agent that may cause damage to a human's health, such as, a dust, fume, biological weapon, chemical agent, any biological material that may replicate and cause disease, like a virus, bacterium, fungus, parasite, protozoa, prion, or the like. In one embodiment, a protective mask is disclosed that includes an impermeable membrane that covers a portion of a user's face, e.g., a user's nose and mouth. In other embodiments, the impermeable membrane may also extend over a user's nose, mouth, and eyes. In many embodiments, at least a portion of the impermeable membrane may be transparent or partially transparent such that the user can see through the impermeable membrane and/or others can see a portion of the user's face through the impermeable membrane. The impermeable membrane may be selected to cover the minimum area of a user's face to prevent inhalation of a damaging agent, e.g., tailored to cover a user's eyes, nose, and mouth, but limited in size and shape for wearability and comfort of a user.

The protective mask also may include a filter cartridge. The filter cartridge includes an air permeable filter element operative to block the passage of damaging agents and suitable for inclusion in a filter cartridge. In some embodiments, the filter cartridge may be removable and/or replaceable. In these embodiments, a user may select a desired filter cartridge, such as one with specific filtering characteristics, depending on the use environment.

In one example, the filter cartridge may be removable from the protective mask or may be pivotable or rotatable relative thereto to allow access and replacement of the filter. For example, the mask may include a cartridge that pivots or releases from a bottom edge of a frame of the mask, which may allow a user to replace just the filter components and reattach the cartridge or may be completely releasable to allow the user to replace the entire cartridge. The replaceable aspects of the filter allows the mask to maintain filtering efficiency and breathability, as well as be adapted to different environments or damaging agents as needed.

The filter cartridge may also include a gasket or seal around a perimeter thereof. For example, the filter may seat within an area defined by the cartridge and a gasket may extend around the perimeter of the cartridge, which acts to seal the cartridge to the frame of the mask or against a user's face, depending on the placement of the cartridge.

The filter cartridge includes a sanitizing emitter suitable to disperse a sanitizing agent into the filter element. The sanitizing agent may deactivate damaging agents as they pass through the filter element, as well as those that are captured by the filter, cleansing the filter and helping to prevent captured elements from affecting a user even if the elements pass through the filter. In many embodiments, the sanitizing emitter is a light emitter that emits light wavelengths as the sanitizing agent. For example, the sanitizing emitter may be a light emitting diode ("LED") configured to emit light wavelengths in an ultraviolet ("UV") portion of the electromagnetic spectrum. UV light may be effective at neutralizing damaging agents by damaging the active biological material of the damaging agent such as its deoxyribonucleic acid ("DNA") or ribonucleic acid ("RNA").

One example of a damaging agent is the severe acute respiratory syndrome coronavirus 2 ("SARS-CoV-2") that causes coronavirus disease 19 ("COVID-19"). SARS-CoV-2 is an RNA virus that may be deactivated by exposure to a sanitizing agent such as UV light. Droplets of sputum, mucus, or other bodily fluids, such as those expelled when an infected person coughs, may contain millions of SARS-CoV-2 particles. Yet, these droplets may be too small for some filter elements to capture. For example, some droplets may be smaller than 200 microns in diameter. By infusing the filter element with a sanitizing agent, such as UV light, virus particles in an infected droplet of sputum may be deactivated such that even if a user of the protective mask inhales an infected droplet that passes through the filter element, the user may not become infected with SARS-CoV-2 and may not develop COVID-19.

In other examples, the protective mask may include a passive filter without the active sanitizing aspects or features. In other words, the filter cartridge may be configured to filter air flow as it travels through the mask via characteristics of the filter material. In one example, the protective mask is also transparent to facilitate user communication, while maintaining a full seal around the perimeter to prevent ingress of damaging agents. The filter cartridge may include a MERV 16 filter. The protective mask may also include anti-fog features within the lens, further ensuring visibility and transparency for the wearer. The protective mask may be secured via a strap, such as a strap positioned and secured via two attachment points (e.g., upper and lower locations on the protective mask) that helps to distribute sealing pressure, as well as anchor the mask over the crown of the user's head.

In various aspects, multiple, substantially, or a number of components of the mask may be formed of transparent or substantially transparent materials. For example, a front impermeable membrane or lens may be transparent, as well as a frame, padding, seals, or the like, may be formed of a clear or substantially clear material. This may allow the mask to become "invisible" or at least less obvious to others in social interactions, allowing people to convey emotions and communicate without the hindrance or obstruction of a mask.

Figure 1:
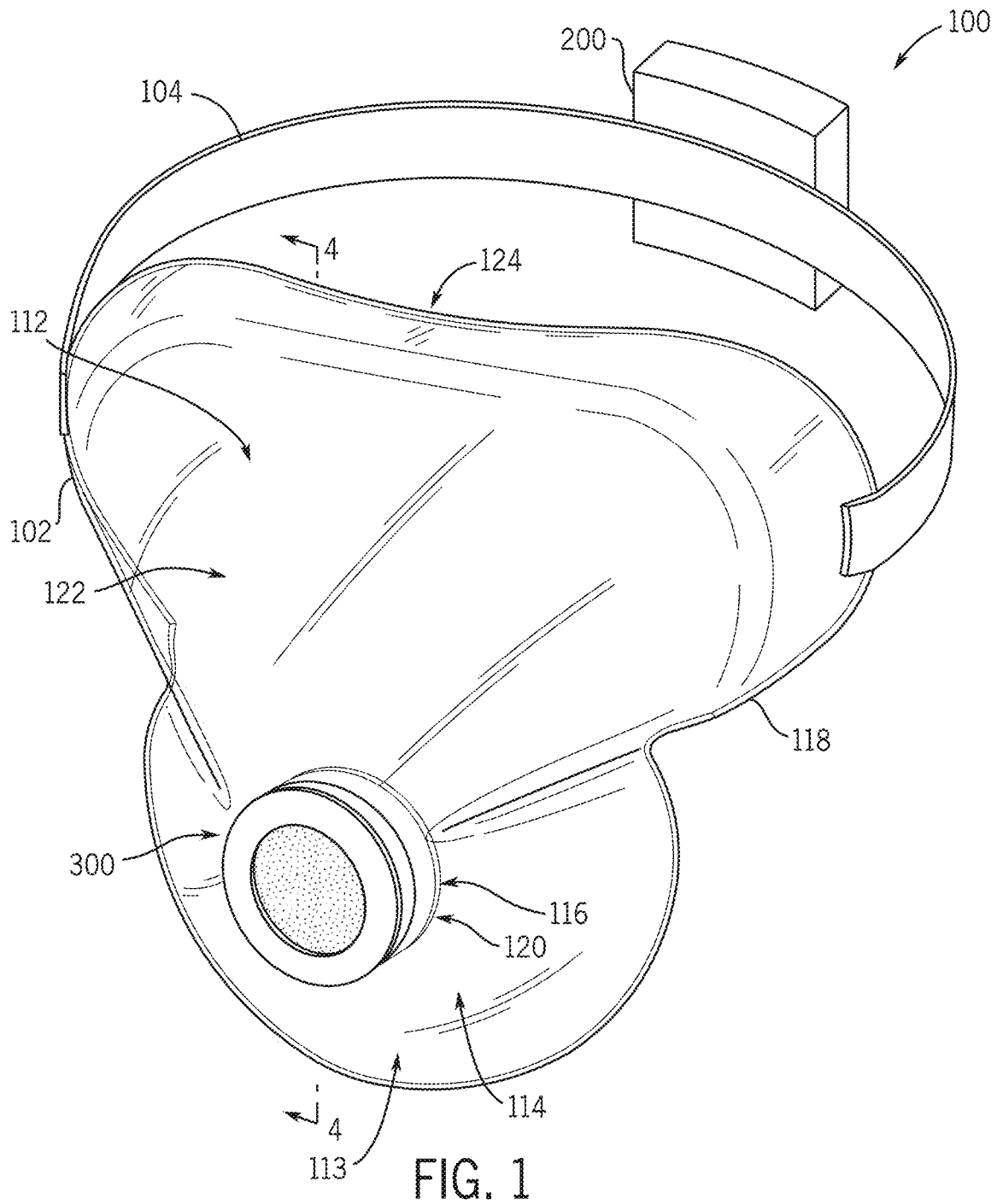
FIG. 1 is an isometric view of an embodiment of a protective mask including a filter cartridge.
Figure 2A:
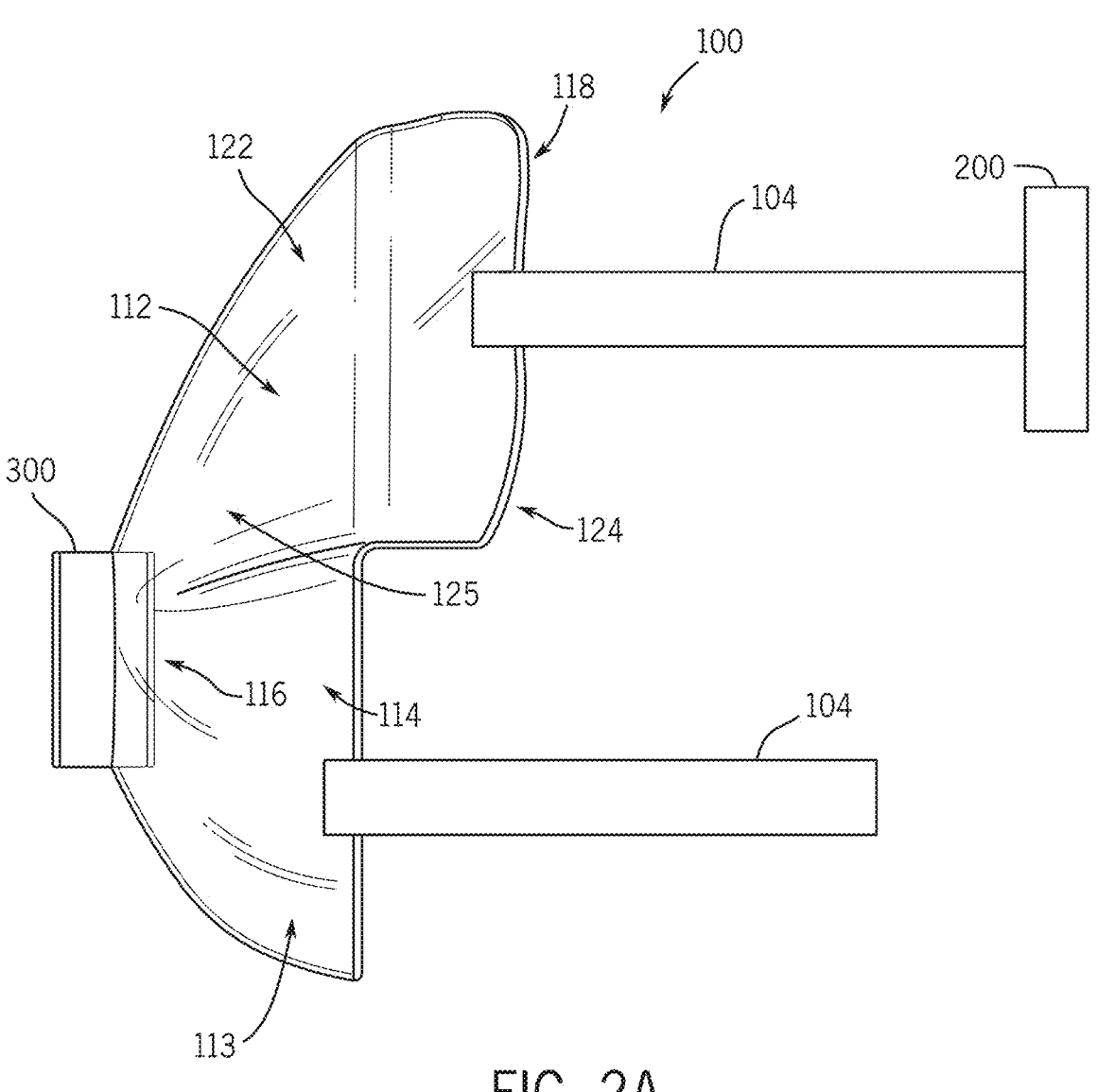
FIG. 2A is a side view of the protective mask of FIG. 1.
Figures 2B, 2C:
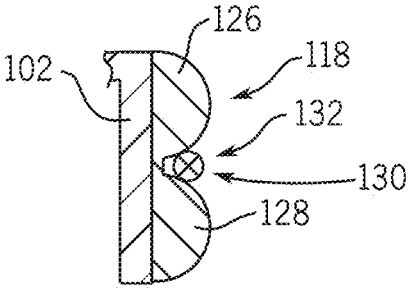
FIG. 2B is a rear view of the protective mask of FIG. 1.
FIG. 2C is a partial cross section of the protective mask of FIG. 1 taken along the section line 2C-2C of FIG. 2B.
Figure 3:
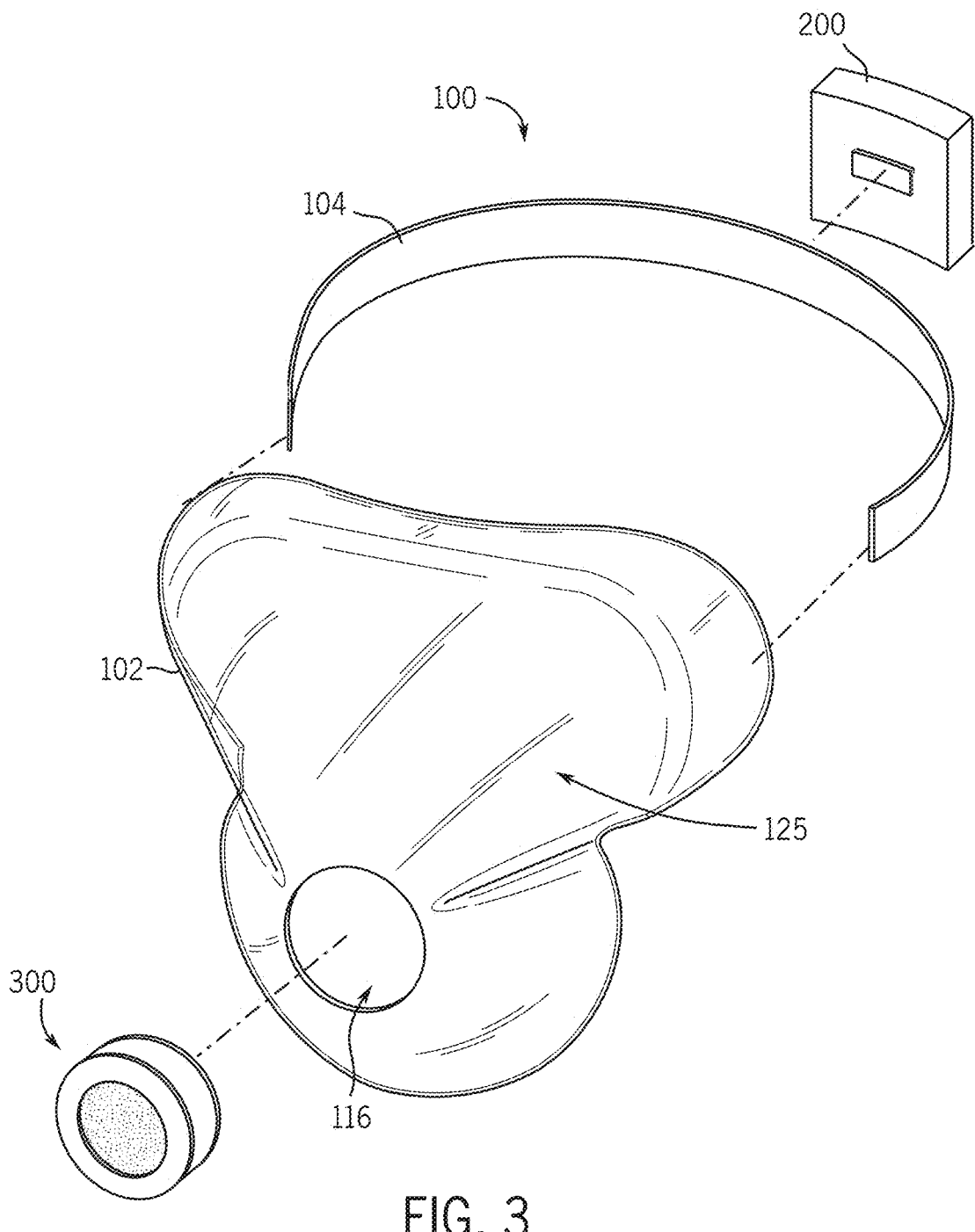
FIG. 3 is an exploded view of the protective mask of FIG. 1.
Figure 4:
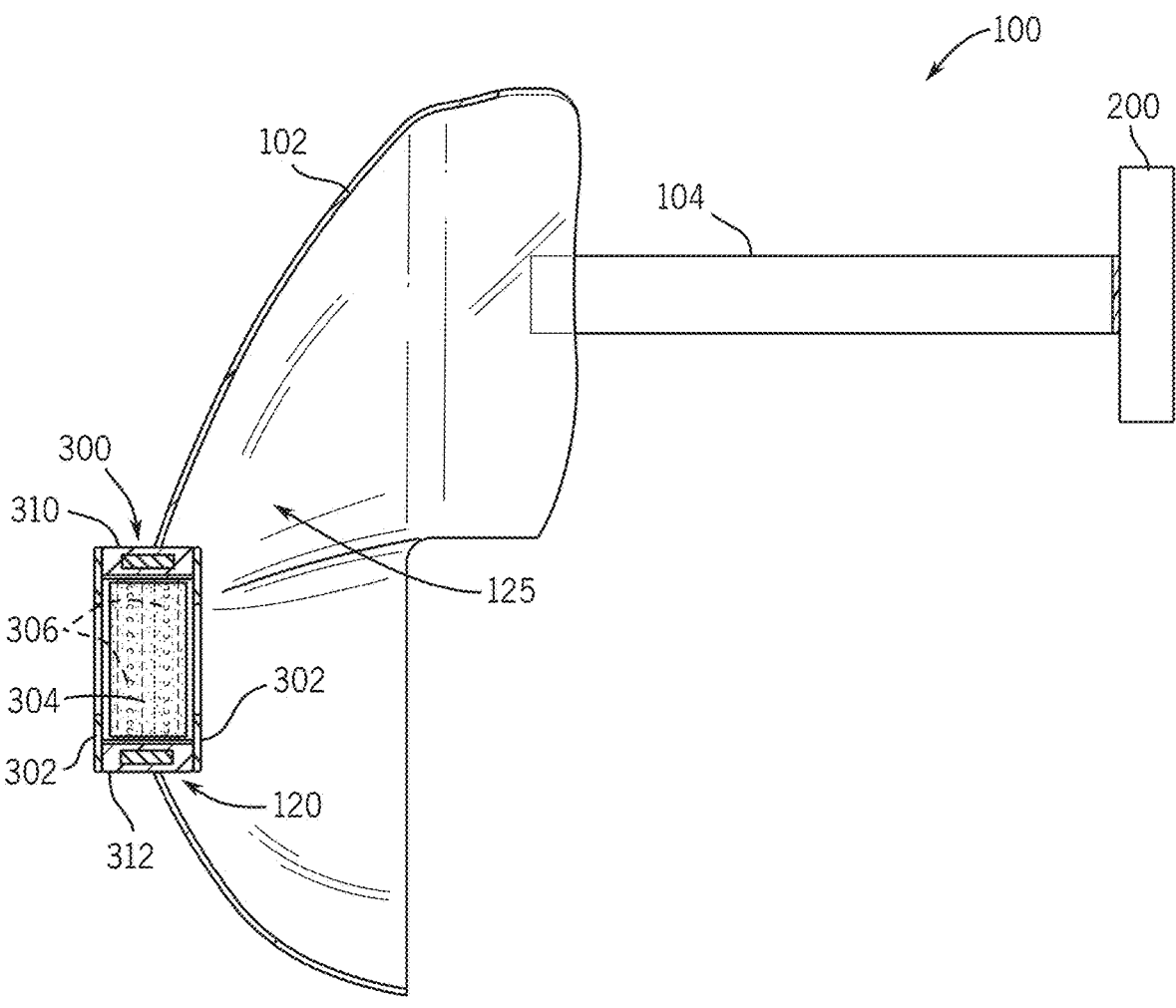
FIG. 4 is a cross section of the view of the protective mask of FIG. 1, taken along section line 4-4 of FIG. 1.
Figure 5:
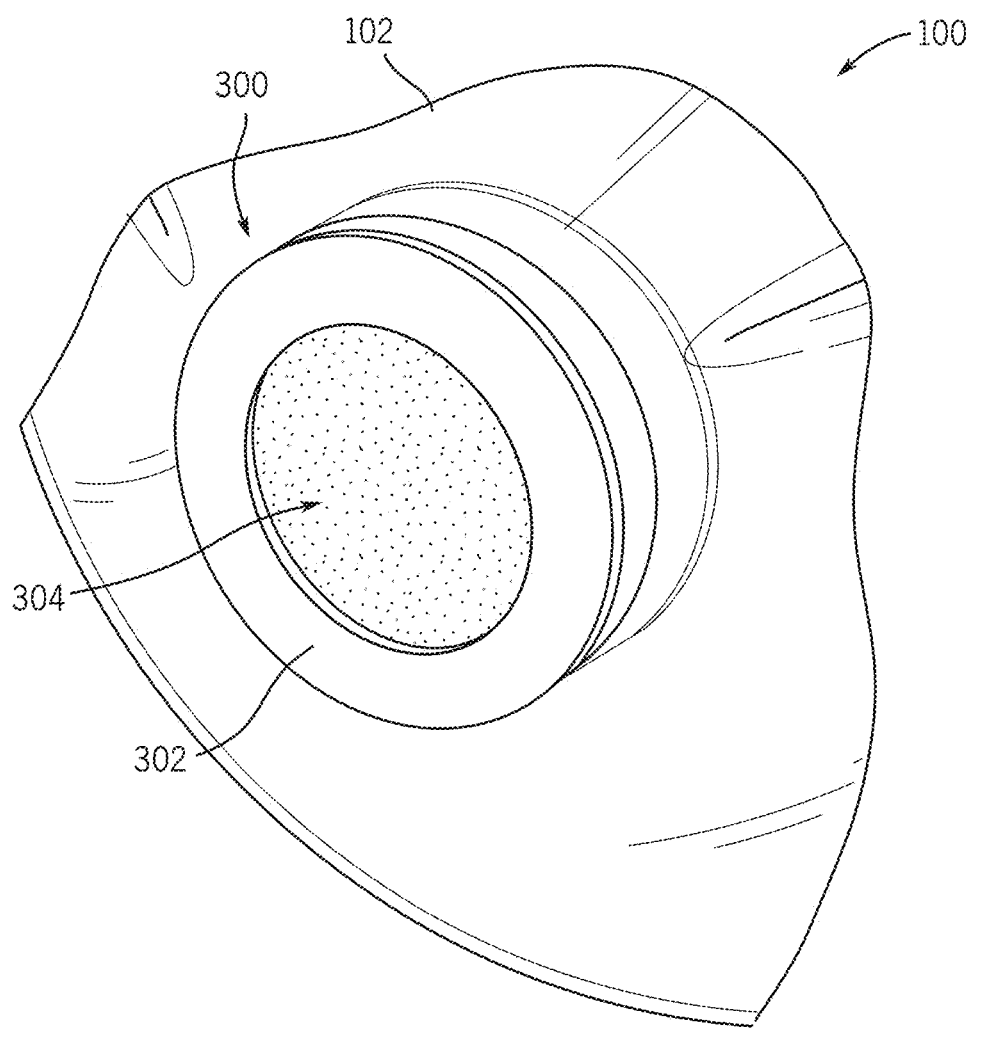
FIG. 5 is a detail view of the filter cartridge of the protective mask of FIG. 1, installed on the protective mask.

FIGS. 1, 2A, and 2B are views of an embodiment of a protective mask 100 including a filter cartridge such as the filter cartridge 300 or 500. Any filter cartridge disclosed herein may be interchangeable with any other filter cartridge disclosed herein. Thus, any references to a particular filter cartridge are to be understood to encompass any other filter cartridge disclosed. For example, the filter cartridges 300 and 500 may be interchanged one with the other and vice versa. The protective mask 100 includes an impermeable membrane 102. In this embodiment, the impermeable membrane 102, which may be considered a lens, includes an eye cover portion 112 (e.g., a portion of the membrane configured to be aligned with or positioned over a user's eyes); a mouth and nose cover portion 114 (e.g., a portion of the membrane configured to be aligned with or positioned over a user's mouth and/or nose); and a chin cover portion 113 (e.g., a portion of the membrane configured to be aligned with or positioned over a user's chin, rather than a user's mouth). In some embodiments, the impermeable membrane 102 may include a mouth and nose cover portion 114 without an eye cover portion 112. The protective mask 100 includes one or more attachment members 104 to selectively attach the protective mask 100 to a user's head. The protective mask 100 may include a sanitizing agent source 200, such as a sanitizing emitter.

The impermeable membrane 102 is shaped to minimally cover access points to a user's respiratory system and optionally the ocular system (e.g., eyes). For example, the impermeable membrane 102 may have a shape that conforms to a user's facial features. For example, the impermeable membrane 102 may have a rounded bottom section with a width corresponding to the width of the user's mouth. The impermeable membrane 102 may taper in toward bridge of a user's nose to form the mouth and nose cover portion 114. The impermeable membrane may expand outward to form the eye cover portion 112. The shape of the impermeable membrane may be functional. For example, the shape may protect the user's face while not protruding excessively to prevent snagging on items near the user's face and also to maintain user comfort. The shape of the impermeable membrane 102 may also be selected for aesthetic elements as well. In one embodiment, the membrane 102 may have a circular bottom shape that tapes inwards to form a rectangular nose bridge, and then expands outwards to form an ovoid or oval shape having a width extending just as long or a bit longer than the spacing between the outer edges of a user's eyes.

Figure 6A:
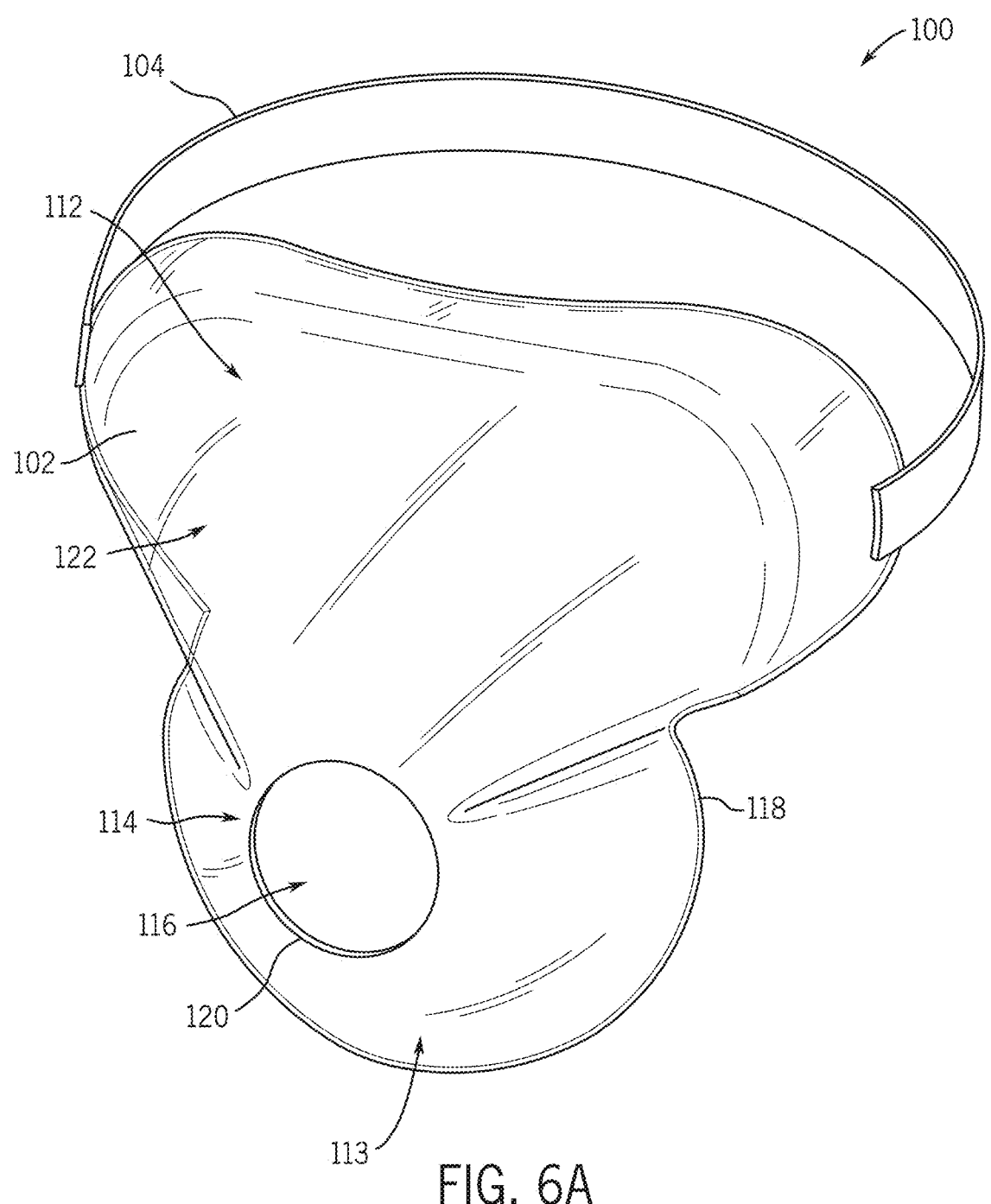
FIG. 6A is an isometric view of the impermeable membrane of the protective mask of FIG. 1.
Figure 6B:
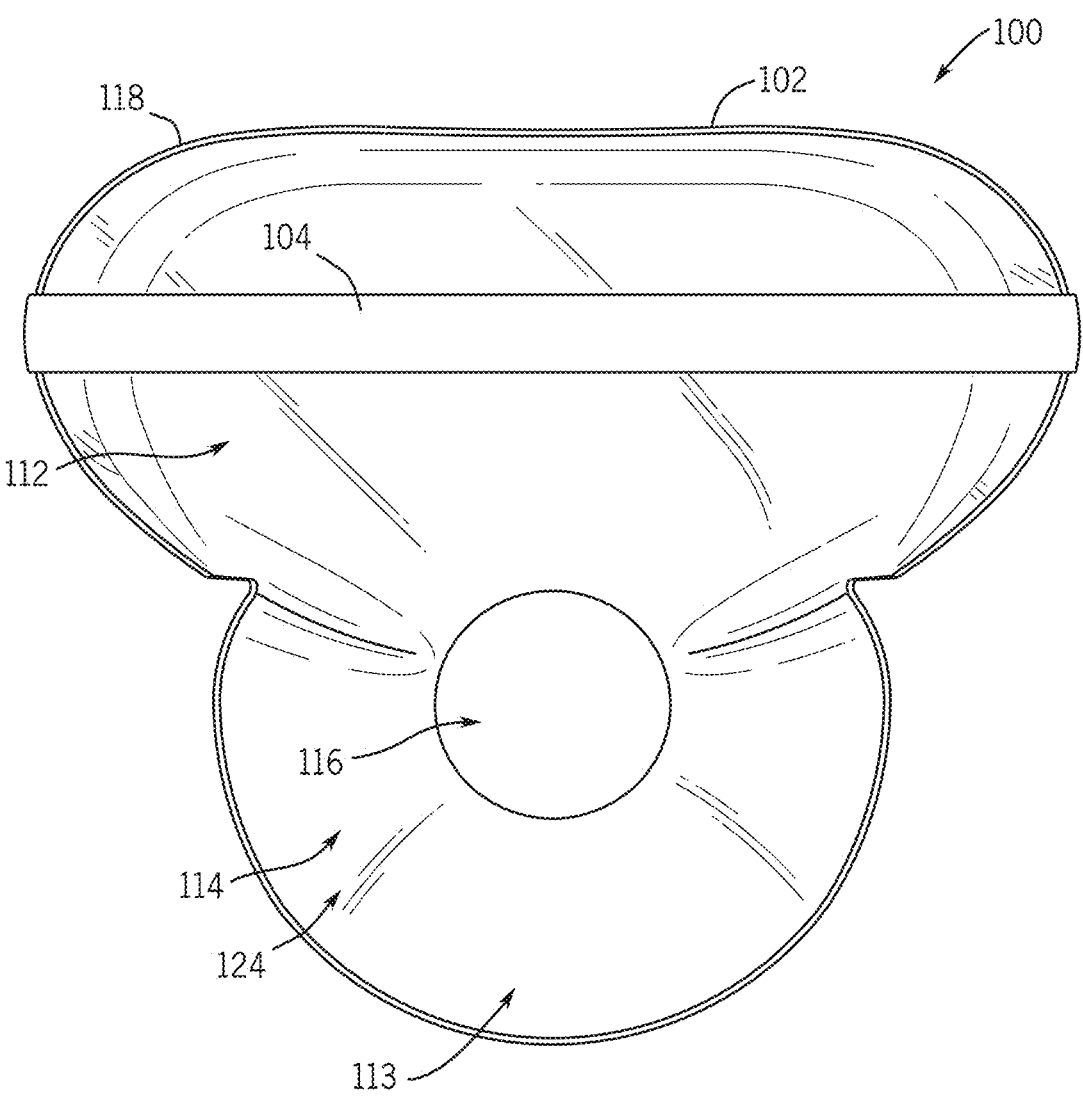
FIG. 6B is a rear view of the impermeable membrane of the protective mask of FIG. 1.
Figure 6C:
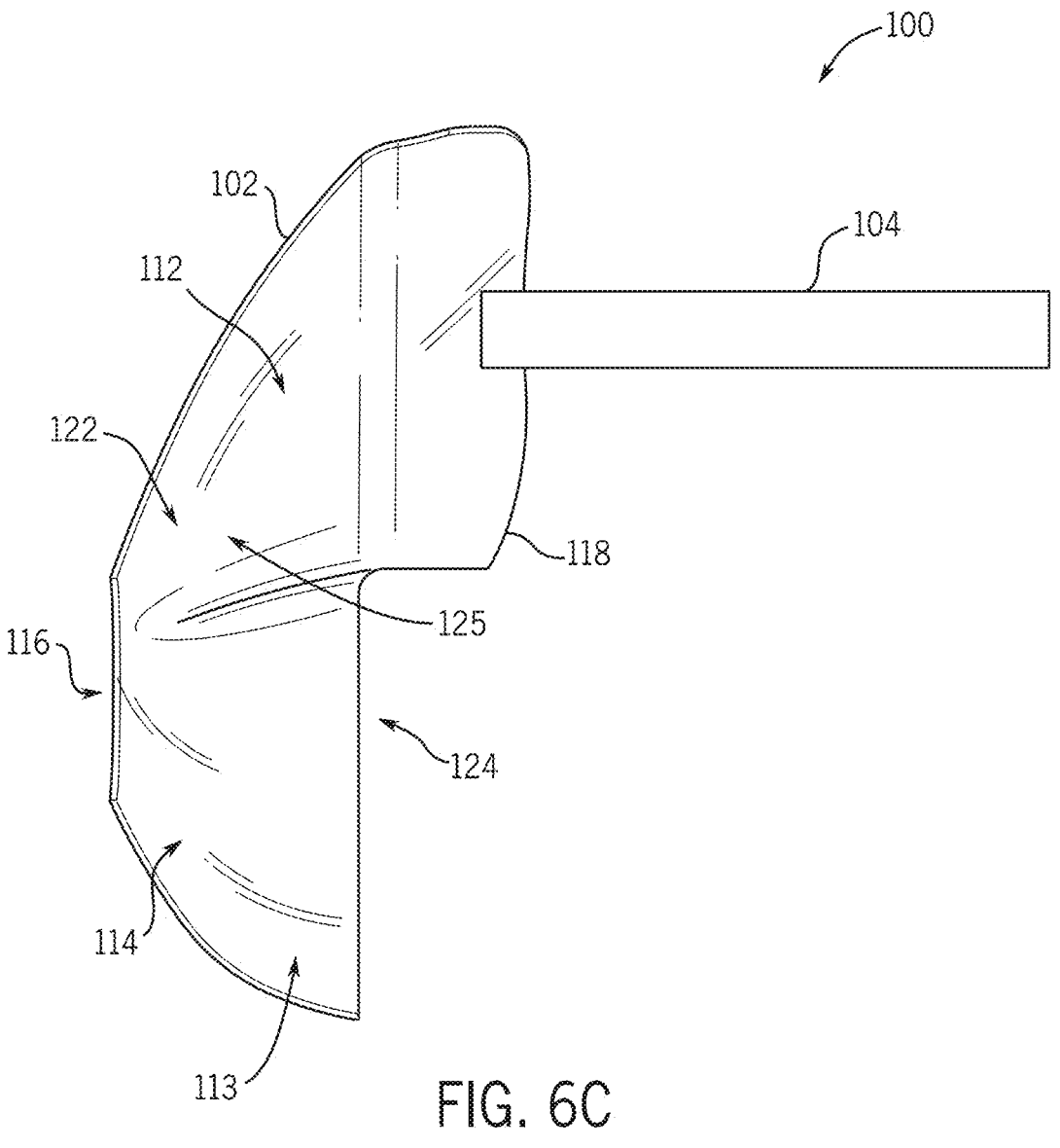
FIG. 6C is a side view of the impermeable membrane of the protective mask of FIG. 1.

With continued reference to FIGS. 1, 2A, 2B, and also FIGS. 6A-6C, the impermeable membrane 102 may have a respiration aperture 116. The respiration aperture 116 may be formed as an aperture that provides an air pathway from an external side 122 or surface of the impermeable membrane 102 to an internal side 124 or surface of the impermeable membrane 102. When a user wears the protective mask 100, an interior space 125 may be formed between the internal side 124 of the impermeable membrane 102 and the user's face. The respiration aperture 116 allows air flow, such that a user can breathe while wearing the protective mask 100. The respiration aperture 116 may define the sole air pathway from the external side 124 of the impermeable membrane 102, such that all air flow into and out of the mask 100 is through the aperture 116. In this manner, as the user respirates (e.g., breathes, sneezes, coughs, or the like), the resulting expelled or inhaled air and other fluids will be directed through the pathway defined by respiration aperture 116. Including a single respiration aperture 116 may maximize the transparent area of the impermeable membrane 102 and improve the user's visibility and/or the visibility of the user's face to others. The respiration aperture 116 may be formed in a desired size and shape, but in some embodiments may be selected to correspond to the shape of the filter cartridge 300, such that the cartridge can seat therein.

Figure 10:
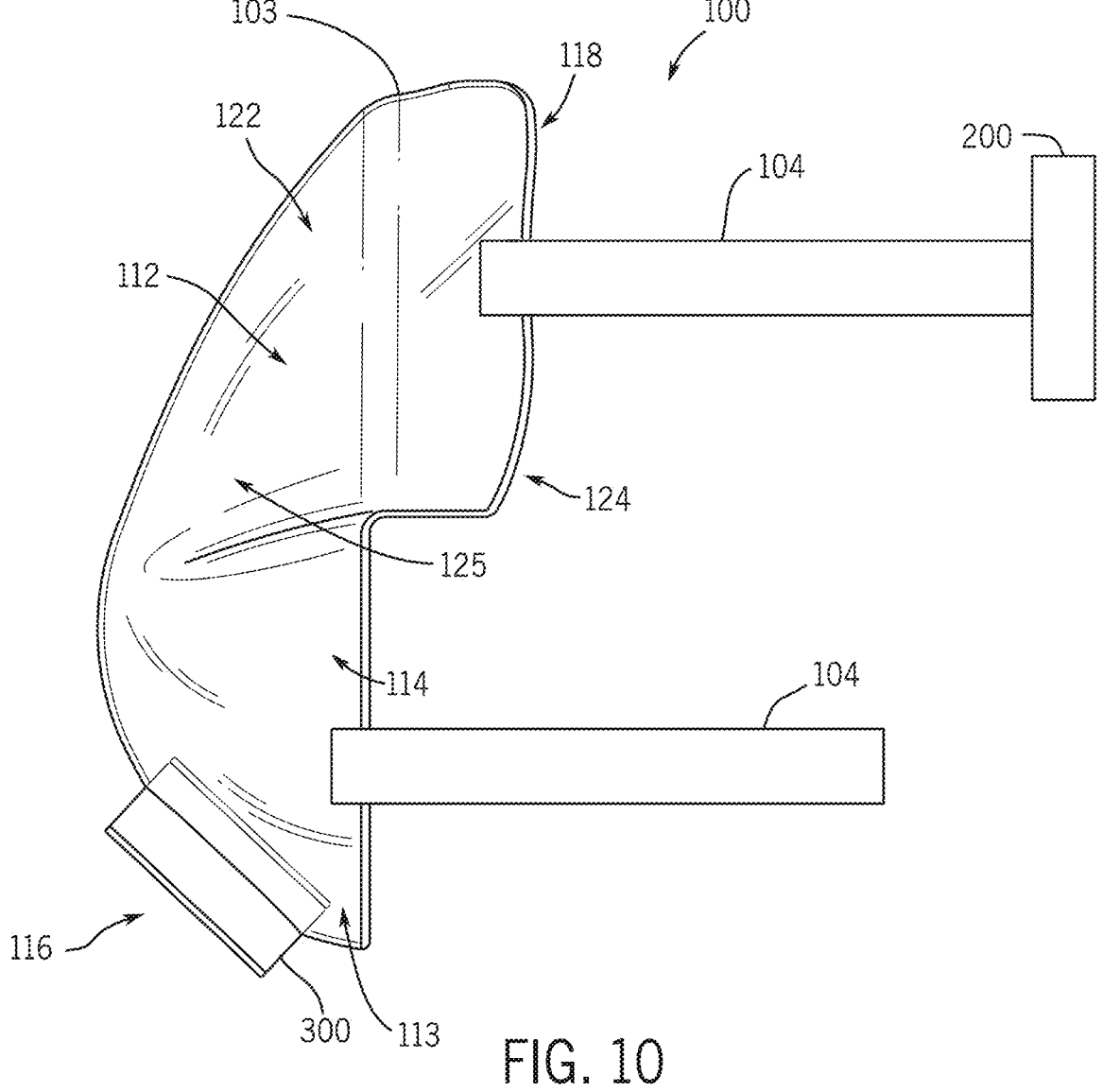
FIG. 10 is a side view of an example of a protective mask.
Figure 11:
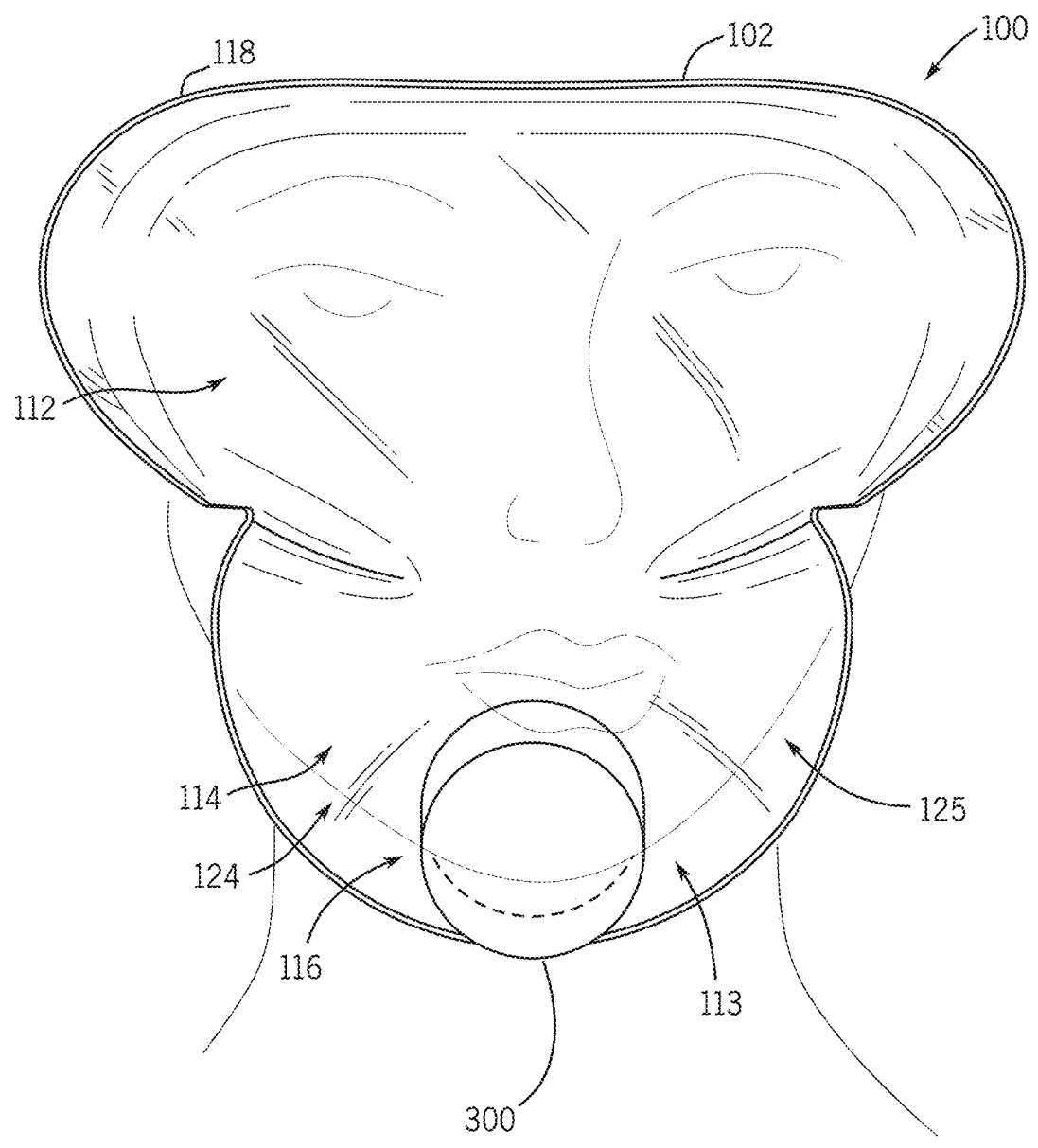
FIG. 11 is an front elevation view of the protective mask of FIG. 10 worn by a user.

The respiration aperture 116 may be situated in any suitable location in the impermeable membrane 102. As shown, the respiration aperture 116 may be positioned in a bottom portion of the membrane between a transition point or below the nasal bridge. The respiration aperture 116 may be placed in other suitable locations. For example, the respiration aperture 116 may be placed lower on the impermeable membrane 102 than as shown, which may allow the filter cartridge 300 to be positioned further from a user's eyes and out of a user's line of sight. As one example, FIG. 10, illustrates an example of a protective mask 100 including an impermeable membrane 103. In many respects, the impermeable membrane 103 is similar to the impermeable membrane 102. The impermeable membrane 103 may differ from the impermeable membrane 102 in the location of the respiration aperture 116 formed in the impermeable membrane 103. For example, the respiration aperture 116 may be positioned in a chin cover portion 113 of the impermeable membrane 103. The respiration aperture 116 may accept any suitable filter cartridge disclosed herein, such as the filter cartridge 300 or 500. As shown for example in FIG. 11, placement of the respiration aperture 116 away from the user's face, such as in the chin cover portion 113 may be beneficial in improving visibility of the user to their surroundings, and/or improving visibility of the user's face to others. For example, with the filter cartridge 300, 500 and respiration aperture 116 in the chin cover portion 113, deaf people may be more easily able to see the mouth of a mask user and able to read the user's lips as the user speaks.

In some embodiments, more than one respiration aperture 116 may be formed in the impermeable membrane 102. For example, a protective mask may include a first respiration aperture 116 in the impermeable membrane 102 with a one-way valve such that as the user breathes in, air is directed through the first respiration aperture 116. The protective mask may include a second respiration aperture 116 with an oppositely oriented one-way valve such that when the user exhales the user's breath is directed out the second respiration aperture 116 and not the first respiration aperture 116. In other embodiments, a protective mask may include more than one respiration aperture 116, each of which may be fitted with a filter cartridge 300. The respiration aperture 116 may be associated with an attachment mechanism 120 suitable to attach to a complementary attachment mechanism 312 of a filter cartridge 300.

The impermeable membrane 102 may be made of any suitable material suitable to conform to a user's face that does not allow the passage of damaging agents therethrough. In many embodiments, the impermeable membrane 102 may limit or prevent the passage of fluids or solid particles therethrough. Additionally, the membrane 102 may be made of a material that can be easily cleaned or sanitized without reducing its impermeability. For example, in some embodiments, the impermeable membrane 102 may be made from plastic (either thermoset or thermoplastic). In many implementations, the impermeable membrane 102 may be made from a transparent or partially transparent plastic such as polyethylene terephthalate ("PET"), polycarbonate (A.K.A. Lexan™), acrylic, polylactic acid, or the like. In such implementations, the transparent plastic may allow a user to see out through the eye cover portion 112 when included. The transparent material may allow others to see the user's face as well, which may be beneficial for security reasons, as well as emotional reasons (e.g., doctors and nurses can better connect with patients when patients can see their entire face).

The sealing element 118 may be disposed around a perimeter of the impermeable membrane 102 so as to seal against the user's face, preventing air and damaging agents from permeating around the border of the impermeable membrane 102. The sealing element 118 may include multiple seals, such as for redundancy, user comfort, improved sealing, or the like. For example as shown in FIGS. 2A-2C, a first seal 126 within the sealing element 118 may be disposed near an outer perimeter edge of the impermeable membrane 102 and a second seal 128 may be disposed inward from the first seal relative to the perimeter edge of the impermeable membrane 102. A channel 130 may be formed between the first and second seals 118, 128. In some embodiments, the sealing element 118 may include two or more adjacent seals. In some embodiments, the sealing element 118 may include two or more overlapping seals. In some embodiments, the sealing element 118 may be disposed along the interior of the impermeable membrane 102, such as between an eye cover portion 112 and a mouth and nose cover portion 114. The sealing element 118 may prevent or discourage a user from touching their eyes, such as in embodiments where the protective mask includes an eye cover portion 112. Likewise the sealing element 118 may discourage users from touching their noses and/or mouths. For example, the sealing element 118 may prevent or discourage a user from inserting a finger beneath the impermeable membrane 102 to touch their face. Thus, the protective mask 100 may prevent a user from introducing a damaging agent to their body through the eyes, nose, or mouth.

In some implementations, an air mover 132, such as a fan, may be disposed within, or in fluidic communication with, the channel 130. The air mover 132 may cause air to move within the channel to cool skin positioned between the channels of the mask 100. The channel 130 and the air mover 132 may be fluidically isolated from the interior space 125 between the internal surface 124 of the mask and the face of a user while wearing the mask 100. The channel 130 and the air mover 132 may also be fluidically isolated from the atmosphere outside the mask 100. The channel 130, seals 126, 128, and the air mover 132 may form a closed-loop cooling area operative to provide cooling to the face of a user wearing the mask while maintaining the seal of the mask against damaging agents. For example, seals 126, 128 may be sealed against the surface of the user's skin, such that air from the air mover 132 cannot reach the skin underneath or adjacent to (on an opposite side) of the seals 126, 128. The air mover 132 acts to stimulate a biological response of the user's skin. In other words, by cooling the skin between the seals 126, 128, the blood flowing to the skin positioned underneath the channel 130 between the seals 126, 128 will be cooled. As blood continues to flow to the area beneath the channel it is cooled.

Thus the air mover 132 may help reduce sweating of the user while wearing the mask 100. The air mover 132 may be powered by the sanitizing agent source in implementations where the source 200 is an electrical power source. In some implementations, the air mover 132 may have its own dedicated power source.

The sealing element 118 may be made of any suitable material adapted to create a seal between a user's face and the impermeable membrane 102. In many embodiments, the sealing element 118 may be selected such that it deforms sufficiently under pressure from the attachment member 104 pressing the impermeable membrane 102 to a user's face to create a seal (e.g., the seal can deform to the user's facial features) but still be comfortable to the user. In many embodiments, the sealing element 118 may be made of a soft durometer elastomer such as natural rubber, latex, silicone, nitrile, or the like. In many embodiments, the sealing element 118 may deform elastically, such that it can be used multiple times, or by different users. In some implementations, the sealing element 118 may deform plastically such that it conforms to a user's face and does not return to its original shape when removed.

The attachment member 104 may be one or more devices suitable to hold the protective mask 100 to the user's face and form a seal between the user's face and the sealing element 118. The attachment member 104 may be attached to the impermeable membrane 102 in such a manner so as to not create a hole in the impermeable membrane 102, and thereby prevent compromising the seal created by the sealing element 118. For example, the attachment member 104 may be attached to an outer surface of the impermeable membrane 102 by any suitable method such as adhesive, a fastener (e.g., button, clasp, hook-and-loop fastener, or the like), welding, brazing, or the like. Such an outer attachment arrangement may prevent the attachment member 104 from compromising the impermeable membrane 102, such as by forming a passage between the external side 122 and the internal side 124 that could allow damaging agents to reach the user's face, bypassing the filter cartridge.

In some embodiments, the attachment member 104 is a strap that fits around a user's head and compresses the impermeable membrane 102 to the user's face. The strap may be adjustable to fit user heads of different sizes and shapes, such as through the use of an elastic element, a cinch, hook-and-loop, clasp, buttons, or the like. In some embodiments, more than one attachment member 104 may be used. For example, one attachment member 104 may be adapted to fit around a user's head, while a second attachment member 104 may be adapted to fit around a user's neck, as shown for example in FIGS. 2A and 2B. As another example, one attachment member may extend around a top of the user's head and one attachment member may extend around a bottom of the user's head. In this manner, the protective mask 100 may be adapted to users with a variety of head shapes and sizes.

With reference to FIGS. 1-5, the filter cartridge 300 may be seated within the respiration aperture 116 such that as a user respirates air and other fluids are drawn through the filter cartridge 300. In some embodiments, the filter cartridge 300 may be permanently fixed to the respiration aperture 116. While in other embodiments, the filter cartridge 300 may be removably attached to the impermeable membrane 102. Such filter cartridges 300 may be replaceable such as at the end of a prescribed period of use (e.g., a number of hours of use, a volume of air passed through, or an expiration date). Filter cartridges 300 may be selectively attached to the impermeable membrane 102 depending on a particular threat or damaging agent of concern. For example, one filter cartridge 300 may be adapted to filter and deactivate SARS-CoV-2, while another filter cartridge 300 may be adapted to filter and deactivate a chemical weapon like a vesicant such as mustard gas. A user may select an appropriate filter cartridge 300 based on the expected threat or use environment. In some embodiments, multiple filter cartridges 300 may be stacked in series to deactivate multiple damaging agents. Such stacked filter cartridges 300 may include interfaces to pass a sanitizing agent from one filter cartridge 300 to another stacked filter cartridge 300. Such filter cartridges 300 may include indicators such as symbols or color codes to indicate the particular damaging agent they are adapted to deactivate.

Figure 7:
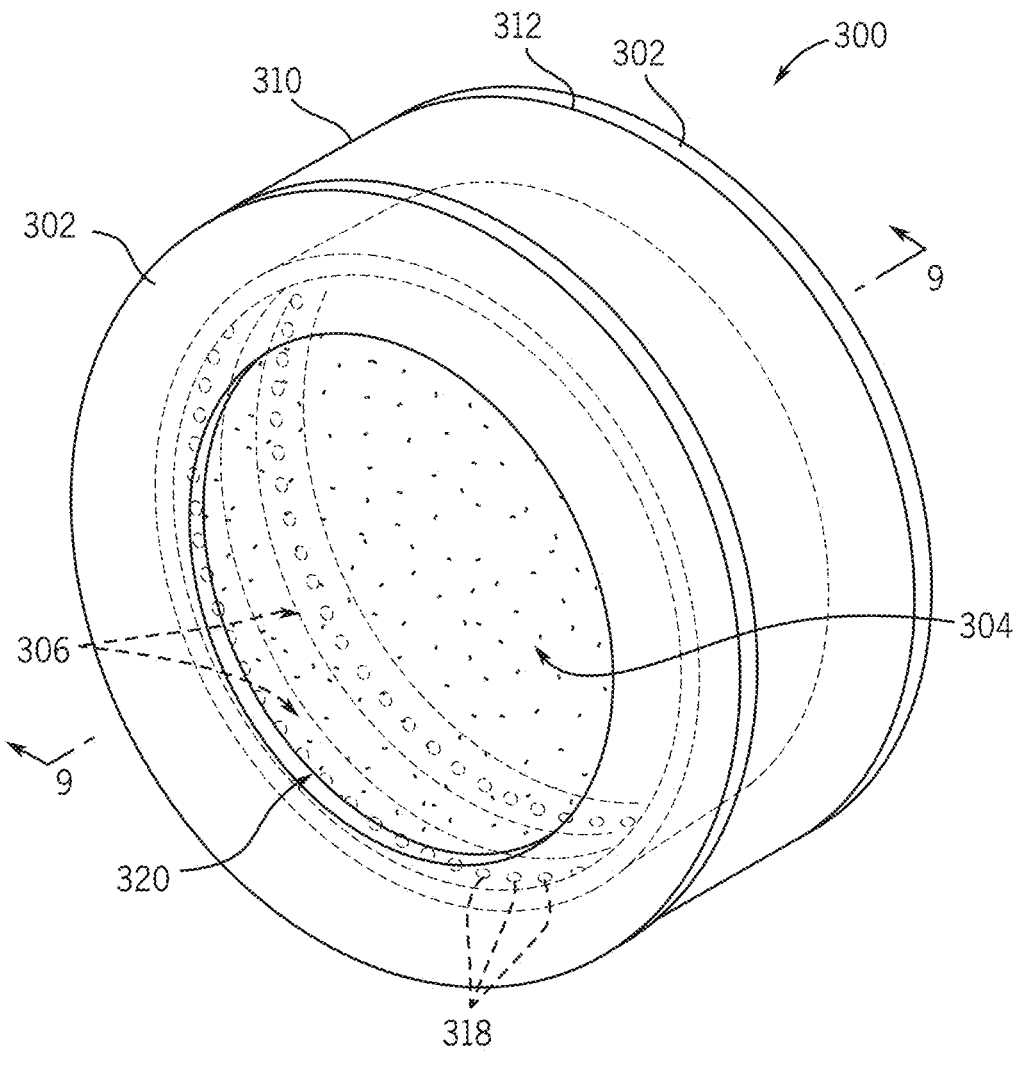
FIG. 7 is a detail view of an embodiment of a filter cartridge suitable for use with the protective mask of FIG. 1.
Figures 8A, 8B:
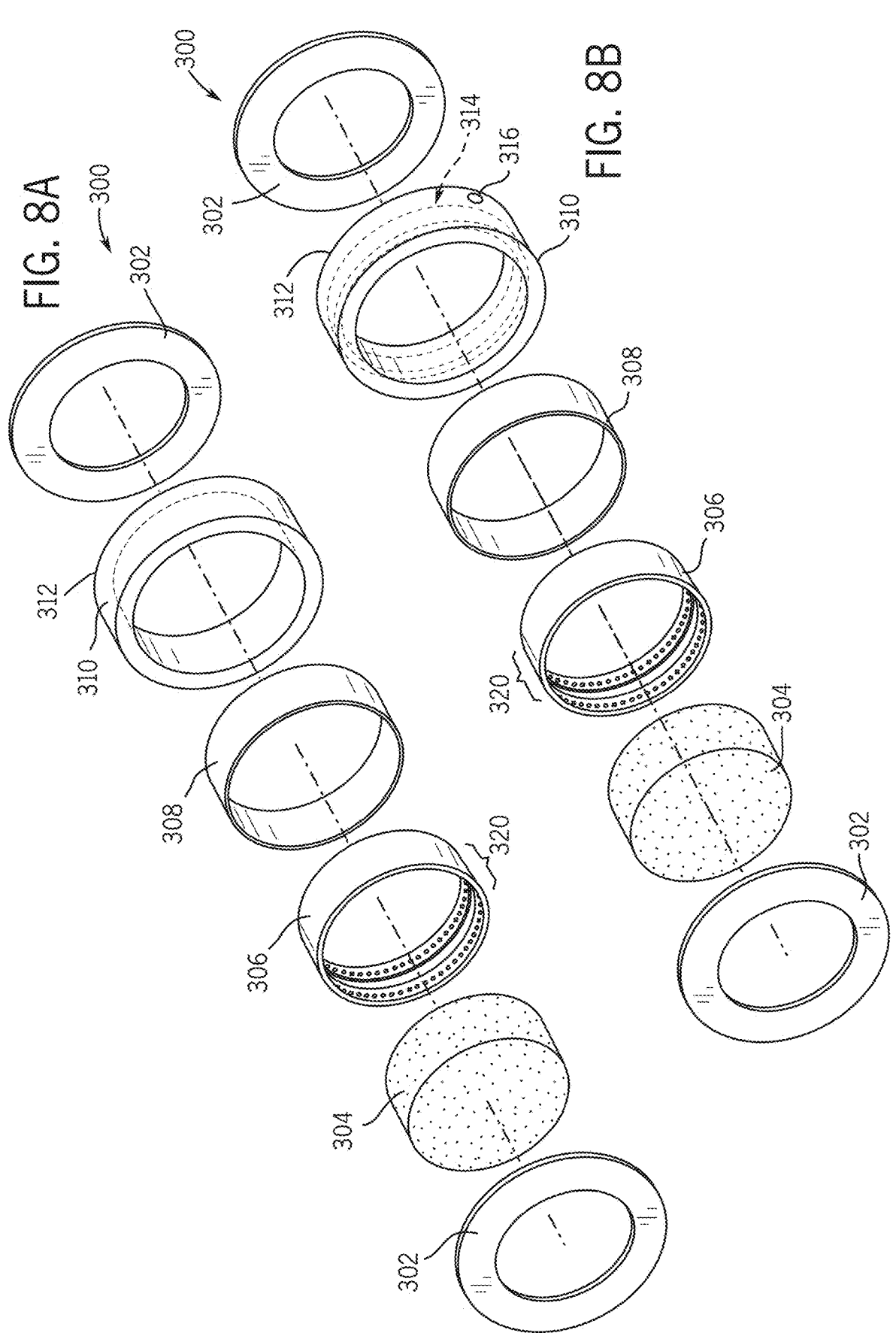
FIG. 8A is an exploded view of the filter cartridge of FIG. 7.
FIG. 8B is an exploded view of an embodiment of a filter cartridge suitable for use with the protective mask of FIG. 1.
Figure 9:
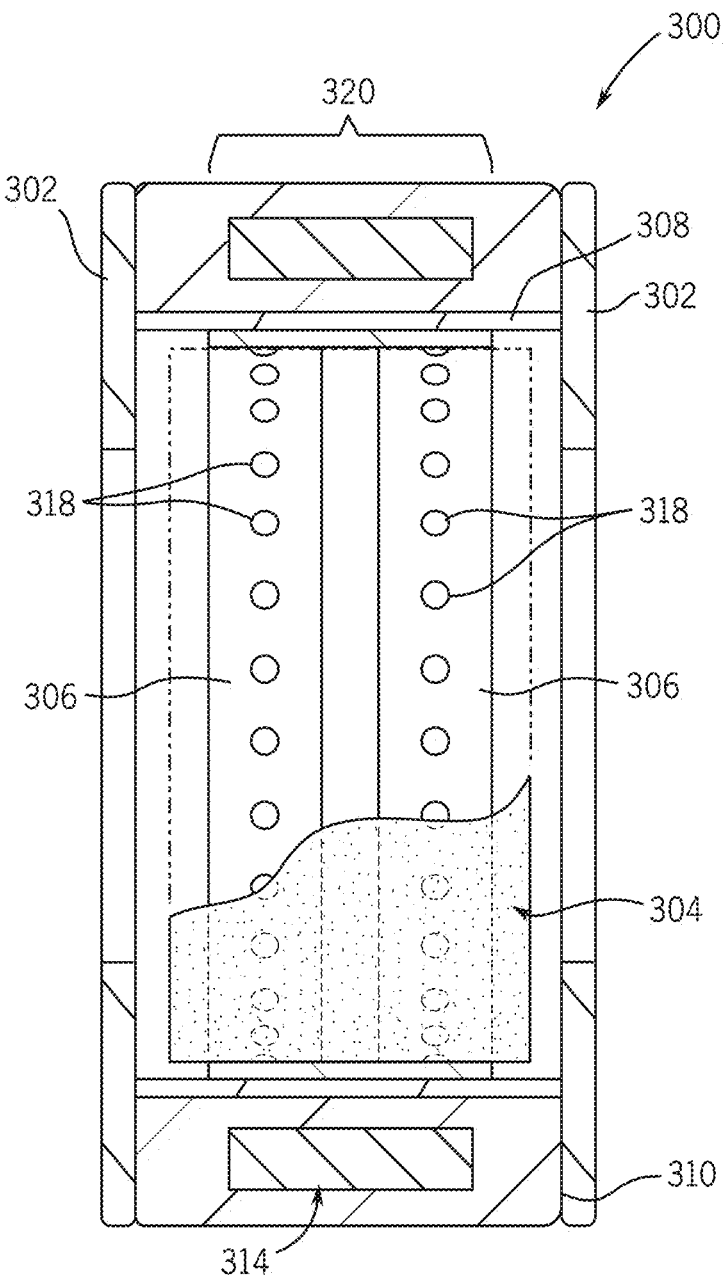
FIG. 9 is a cross section of the filter cartridge of FIG. 8B.

Turning to FIGS. 7-9, an example of a filter cartridge 300 is shown. The filter cartridge 300 includes a filter element 304, sanitizing emitter 306, one or more containment elements 302, a containment element 308, and a cartridge housing 310 that supports the other components of the cartridge. While in the example shown in FIGS. 7-9 the filter cartridge 300 is substantially cylindrical, other suitable shapes may be used, such as cubes, prisms, parallelepipeds, irregular shapes, and the like. The shape of the filter cartridge 300 may be selected based on the location and size of the respirator aperture.

The shape of the filter cartridge 300 may be selected to optimize permeation of the sanitizing agent through the filter element 304. For example, a filter element 304 with a circular cross section may have the smallest perimeter for a given size. Thus, relatively fewer emitters may be positioned around the perimeter and permeate the filter element 304 with a sanitizing agent relative to a filter element with a non-circular cross section. For example, a filter element with a rectangular cross section may have a larger perimeter than a similarly sized filter element with a circular cross section. Likewise, a filter element 304 with a circular cross section may simplify the uniform permeation of the filter element 304 with the sanitizing agent. For example, in a filter element 304 with a circular cross section, sanitizing emitters 306 or emitting elements 318 may be placed uniformly from the center of the filter element 304. In some examples, the sanitizing emitters 306 or emitting elements 318 may be approximately equidistant from the center of the filter element 304. Thus the sanitizing emitter 306 may be able to more uniformly permeate the filter element 304 relative to an element with a non-circular cross section.

The cartridge housing 310 supports the other elements of the filter cartridge 300, and may include an attachment mechanism 312 to attach the cartridge housing 310 to the impermeable membrane 102, such as at a complementary attachment mechanism 120. A seal may be formed between the cartridge housing 310 and the impermeable membrane 102 that prevents the passage of damaging agents. In many embodiments, the seal may prevent the passage of fluids and/or solid particles. In some embodiments, the attachment mechanism 312 may be removably coupled to the impermeable membrane 102. For example, the attachment mechanism 312 may include threads that rotatably mate with complementary helical threads of the attachment mechanism 120, e.g., helical threads. In some implementations, one of the attachment mechanism 120 or the attachment mechanism 312 may include part of a bayonet mount, such as fingers, and the other of the attachment mechanism 120 or the attachment mechanism 312 may include a complementary portion of a bayonet mount, such as tangs or slots that engage the fingers. In other embodiments, the attachment mechanism 312 may be permanently coupled to the impermeable membrane 102. For example, the attachment mechanism 312 and the attachment mechanism 120 may be welded, adhered, brazed or otherwise joined. In some implementations, the attachment mechanism 312 or the attachment mechanism 120 may include a magnetic element adapted to releasably couple to the other of the attachment mechanism 312 or the attachment mechanism 120. In some implementations, a cartridge housing 310 may be unitarily formed with the impermeable membrane 102, such as in a single continuous piece.

The filter element 304 may be any element suitable to allow the passage of air, yet block or filter the passage of particles, such as particles of damaging agents. The filter element 304 may trap particles of a damaging agent in the filter element 304, thereby preventing the spread of the particles to or from a user of the protective mask 100. Due to the density, the filter element 304 may increase the dwell time of particles of a damaging agent in the filter element 304, even if the particles ultimately pass through. Thus, the filter element 304 may increase the time during which a damaging agent is exposed to a sanitizing agent, thereby increasing the efficacy of the sanitizing agent at deactivating the damaging agent.

A filter element 304 may be adapted to filter a percentage of particles of a certain size. For example, various filter elements may be rated by the National Institute for Occupational Safety and Health ("NIOSH") for efficacy at filtering particles of certain sizes. In one example, a filter element 304 may be rated as "N95" meaning the filter element 304 can filter at least 95% of airborne particles 0.3 microns or above. Likewise an "N100" filter element can filter 99.97% of particles 0.3 microns or above. In other examples, a filter element 304 may be rated with a minimum efficiency reporting value ("MERV") rating. For example, a filter element 304 with a MERV rating of MERV 13 with a 90% efficiency for filtering particles between 3 and 10 microns in size (such as mold spores, dusting aids, and cement dust). In another example, a filter element 304 may have a MERV rating of MERV 4 with a 20% efficiency for filtering particles between 3 and 10 microns in size. In some implementations, the filter element 304 may filter particles above 50 microns in size.

The filter element 304 may be made of any suitable structure and/or material that can trap, block, or slow the passage of a damaging agent. In some embodiments, the filter element 304 may be made of a woven fabric having a warp and weft formed of filaments of a material. In some embodiments, the filter element 304 may be formed from a non-woven fabric. For example, a filter element 304 may include one or more layers of a spun bonded or melt blown material. In some embodiments, the filter element 304 may include a foam such as an open or closed cell foam. In some embodiments, the filter element may be pleated, so as to increase filtering surface area. Combinations of suitable structures may be used. Some examples of suitable materials include natural materials like cotton, wool, jute, flax, or hemp. Synthetic materials such as plastics like polypropylene, nylon, polyester, nylon, rayon, or the like may be used. In some embodiments, the filter element 304 may include an adsorbing or absorbing material such as activated carbon or the like. Combinations of these or other materials may be used.

In some implementations, a filter element 304 may include two or more materials with different filter ratings. For example, a filter element 304 may include a light pre-filter for large particles, and a second main filter for smaller particles. All or part of a filter element 304 may be removable from a filter cartridge 300. For example, if a filter element 304 has reached the end of its life, it may be removed from a filter cartridge 300 and cleansed or replaced with another filter element 304. Likewise, if a pre-filter is used, the pre-filter may be removed from the filter cartridge 300 and cleaned or replaced with another pre-filter. A filter element 304 may be effective at trapping damaging agent particles even if the sanitizing agent is broken, depleted, or otherwise unavailable.

The sanitizing emitter 306 may be any element that emits a sanitizing agent operative to deactivate a damaging agent. In many implementations, the sanitizing emitter 306 may be directly adjacent to the filter element 304. For example, the sanitizing emitter may be in direct contact with the filter element 304. Direct contact may enable uniform and thorough permeation of the sanitizing agent into the filter element 304. In one example, as shown in FIGS. 7-9, the sanitizing emitter 306 is an array of UV LEDs operative to deactivate damaging agents. Other suitable UV emitters may be used, such as a fluorescent tube. For example, as shown in FIGS. 5, 7, 8A, 8B, and 9, the LED array is in the form of one or more rows 320 disposed around the outer circumference of the filter element 304 to project a sanitizing agent in the form of UV light into the filter element 304. The rows 320 may be parallel to one another. The rows 320 may have one or more individual emitting elements 318 arranged in lines or other arrangements. In implementations where the filter element 304 has a circular cross section, the rows 320 may be one or more rings, which may be parallel to one another. For example, emitting elements 318 such as LEDs may be spaced apart from one another inline along the row 320. The sanitizing emitter 306 may surround the exterior perimeter of the filter element 304, such as a circumferential edge of the filter element 304. When more than one ring of LEDs is used, the rings may be disposed such that the LEDs are staggered. Such staggering may enable more uniformly permeation the filter element 304 with the sanitizing agent.

In some implementations, multiple LEDs may be adapted to emit different wavelengths of light. For example, some LEDs may be adapted to emit light effective to deactivate viruses, while other LED may be adapted to emit light adapted to kill bacteria, and so on.

In many implementations, the UV light may have a wavelength in the range of 220-280 nanometers. In some implementations, the UV light may have a wavelength up to approximately 400 nanometers. In a preferred implementation, the UV light may have a wavelength of approximately 264-265 nanometers. As damaging agents pass into the filter element 304, they may become exposed to the UV light and may be deactivated, whether they ultimately become trapped in, or pass through, the filter element 304. Thus, the sanitizing agent, such as UV light, may prevent the filter element 304 from harboring damaging agents.

The filter cartridge 300 may include one or more containment elements that help to prevent the sanitizing agent from exiting the filter cartridge 300. For example, as shown in FIGS. 5, 7, 8A, 8B, and 9, the filter cartridge 300 may include one or more containment elements 302 and a containment element 308. In the embodiment where the sanitizing agent is light, the containment element 302 and the containment element 308 may be made of a material that absorbs and/or reflects the light to prevent it from escaping from the filter cartridge 300. For example, the containment element 302 and/or the containment element 308 may be made from a UV absorbing or reflecting polymer, aluminum sheet, or other suitable materials. In the example where the light is UV light, it may be important to help reduce UV light exiting the emitter from impacting the skin or eyes of the user or of others nearby. The containment element 308 may be disposed transversely outward in a direction from an edge of the filter element 304 toward the cartridge housing 310 relative to the sanitizing emitter 306. Thus, the containment element 308 may surround an exterior perimeter of the sanitizing emitter 306 and contain the sanitizing agent in a transverse direction relative to the filter element 304. A containment element 302 may be disposed outwardly in a longitudinal direction from the internal surface 124 toward the external surface 122 of the impermeable membrane 102 relative to the filter element 304. Another containment element 302 may be disposed inwardly in a longitudinal direction from the external surface 122 toward the internal surface 124 of the impermeable membrane 102 relative to the filter element 304. Thus, the containment elements 302 may contain the sanitizing agent in longitudinal directions relative to the filter element 304.

In other examples, a sanitizing agent may be a fluid operative to deactivate a damaging agent, such as a disinfectant liquid. The sanitizing emitter 306 emits the sanitizing agent to permeate the filter element 304. For example, a solution of ethanol or sodium hypochlorite may be applied by an emitter such as a nozzle or sprayer to the filter element 304.

In many implementations, the filter element 304 may form a seal between the internal walls of the cartridge housing 310, the containment element 308, and/or the sanitizing emitter 306. For example, an outer dimension of the filter element 304 may be larger than in inner dimension of the sanitizing emitter 306. The filter element 304 may thus have an interference fit with the cartridge housing 310, the containment element 308, and/or the sanitizing emitter 306. In some implementations, a seal may be placed between the filter element 304 and the cartridge housing 310, the containment element 308, and/or the sanitizing emitter 306. For example when the sanitizing agent is light, a light-transmitting material may be placed between the sanitizing emitter 306 and the filter element 304. For example, a fused quartz material that transmits UV light may be placed between the cartridge housing 310, the containment element 308, and/or the sanitizing emitter 306 and the filter element 304.

The sanitizing agent source 200 contains a source for the sanitizing agent. In many implementations, the sanitizing agent source 200 is a power source such as a primary or secondary battery adapted to power a sanitizing emitter such as a light source. In other implementations, the sanitizing agent source 200 may be a reservoir of a sanitizing agent such as a sanitizing fluid, and a mechanism such as a pump, fan, compressor, or valve adapted to dispense the sanitizing fluid to the sanitizing emitter. The sanitizing agent source 200 is operatively coupled to the sanitizing emitter to supply the emitter. For example, when the sanitizing agent source 200 is a power source, the sanitizing agent source 200 may be operatively coupled to the sanitizing emitter by a wire to carry electrical power. In another example, when the sanitizing agent is a fluid, the sanitizing agent source 200 may be coupled to the sanitizing emitter by a conduit such as a tube, pipe, or hose.

The sanitizing agent source 200 may be disposed in any suitable location on the protective mask 100. For example, the sanitizing agent source 200 may be associated with an attachment element as shown for example in FIG. 1. In other examples, such as shown in FIG. 8B and FIG. 9, the sanitizing agent source 200 may be disposed within the cartridge housing 310 of the filter cartridge 300. For example, the sanitizing agent source 200 may be a power source 314 disposed within the cartridge housing 310. The power source 314 may be a primary (single use) battery, or may be a secondary (rechargeable) battery such as a lithium battery. The power source 314 may be recharged via a power connector 316 adapted to receive power from an external power source such as an external battery, alternating current adapter, wall plug, or the like. The sanitizing agent source 200 may be operated by an actuator such as a switch or valve that controls the supply of the sanitizing agent.

In some implementations, the sanitizing agent may enable the use of a less dense filter element 304 (i.e., a filter element with a lower filtration efficiency) while maintaining a desired level of deactivation of a damaging agent. As a lower efficiency filter element 304 is more porous than higher efficiency filter elements, the lower the efficiency, the easier it may be easier for a user to breathe while wearing the protective mask 100. A lower efficiency filter element 304 may also be less expensive and/or have a longer serviceable life than a higher efficiency filter element 304, which can become prematurely plugged and inoperable to breathe through. Thus, the sanitizing emitter and sanitizing agent may increase user comfort, allow a user to participate in activities with a higher respiration rate than a higher efficiency filter element 304 (e.g., strenuous physical activity, stressful situations, or the like), or increase the life of the protective mask 100.

In the assembled filter cartridge 300, the containment element 308 may be inserted into the cartridge housing 310. The sanitizing emitter 306 may be inserted inside the containment element 308. The filter element 304 may be fitted into the cartridge housing 310 inward of the sanitizing emitter 306. The filter element 304 may be inserted snugly against the sanitizing emitter 306. As such, the sanitizing emitter 306, including individual emitting elements 318, may be directly adjacent to the filter element 304. The containment element 302 may be assembled over the filter element 304.

Figure 12:
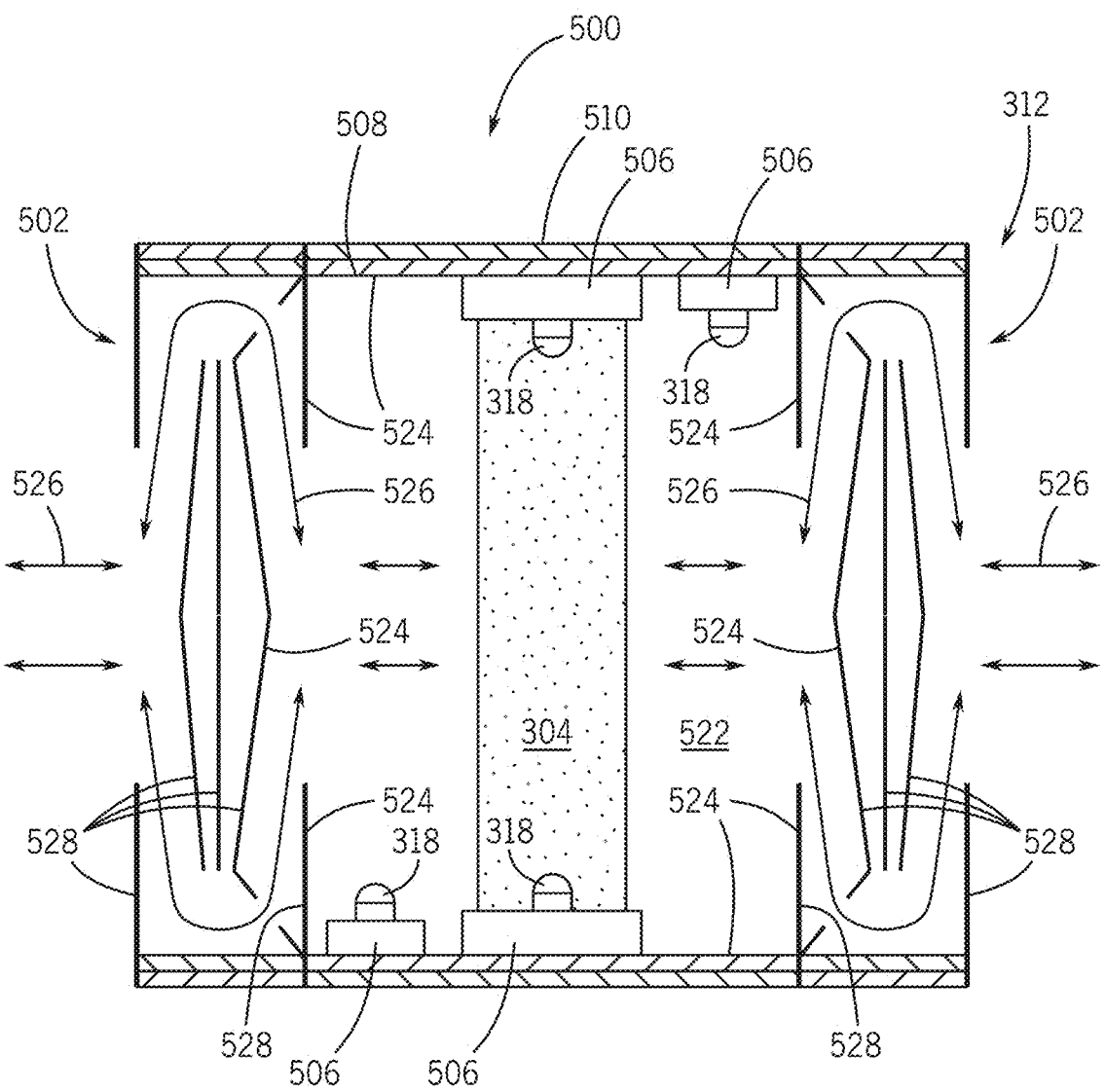
FIG. 12 is a cross section of a filter cartridge.

FIG. 12 shows an example of a filter cartridge 500. The filter cartridge 500 may be similar to the filter cartridge 300, but may include varied containment structures. The filter cartridge 500 includes a filter element 304, sanitizing emitter 306, emitting elements 318, one or more containment elements 502, a containment element 508, an attachment mechanism 312, and a cartridge housing 510 that supports the other components of the filter cartridge 500. These elements may be similar to analogous elements of the filter cartridge 300 described herein.

The containment element 502 includes one or more containment structures 528 disposed at opposing ends of the housing 510. The containment structures 528 contain the sanitizing agent within the filter cartridge 500. For example, the containment structures may reflect and/or absorb the sanitizing agent to contain the agent within the filter cartridge 500. The containment structure 528 of a containment element 502 may form a tortuous path 526 that allows air to pass through the containment element 502, but which blocks a sanitizing agent emitted by the sanitizing emitter 506 from passing through the containment element 502. In some implementations, the containment structure 528 may be formed as a baffle 528. In some implementations, a containment structure 528 may form an aperture 530 therein. In some examples, a containment structure 528 may be a thin sheet of a material that blocks, reflects, filters, and/or absorbs UV light. For example, a containment structure 528 may be formed of metal, opaque plastic, a metallized film, a dyed plastic substrate, combinations of these or similar materials that can structurally form a baffle 528 and can contain UV light.

The filter cartridge 500 may have a chamber 522 formed therein and configured to contain the filter element 304 and/or one or more sanitizing emitters 506. The housing 510 and/or one or more of the containment structures 528 may form the chamber 522 within the filter cartridge 500. For example, the housing 510 may form a circumferential wall of the chamber 522 and containment structures 528 may form opposing ends of the chamber 522. The chamber 522 may house or contain the filter element 304 and one or more sanitizing emitters 506. In many embodiments, the sanitizing emitter 506 may be in contact with the filter element 304. In some embodiments, a sanitizing emitter 506 may be disposed within the chamber 522, separately from the filter element 304, such as sanitizing emitters 506b.

In some implementations, air may flow into a first aperture 530a, along the tortuous path 526 around a baffle 528 and out of an aperture 530b disposed in the interior of the filter cartridge 500, such as an aperture 530b adjacent to the chamber 522. Air may continue into the chamber 522, through the filter element 304, and to an opposite end of the chamber 522 from which the air entered. As air passes through the chamber 522, the air may be sanitized by the sanitizing agent, and/or filtered by the filter element 304. Air may continue through the aperture 530c, around a baffle 528 and exit the filter cartridge 500 at an aperture 530d. The flow of air may be reversed as the user breathes in and out, the air being sanitized in both directions as it flows through the cartridge.

In some implementations, the chamber 522 may be a reflective chamber 522 operative to reflect the sanitizing agent emitted by a sanitizing emitter 506. For example, the housing 510 and/or a baffle 528 may have a reflective property or have a reflective coating or layer 524 disposed thereon. For example, in implementations where the sanitizing agent is UV light, the reflective layer 524 may reflect the UV light within the reflective chamber 522. Reflections of the sanitizing agent within the reflective chamber 522 may increase the contact of the sanitizing agent with harmful agents. For example, a light beam may reflect hundreds, thousands, or even more times within the reflective chamber 522, with each reflection increasing the probability that the sanitizing agent may contact and neutralize a harmful agent. A reflective chamber 522 may enable the use of fewer sanitizing emitters 506 or a smaller sanitizing agent source 200 than a comparable filter cartridge without a reflective chamber. As discussed above, reflections of the sanitizing agent within the chamber 522 may increase the likelihood that a harmful agent may be neutralized by the sanitizing agent. Thus, fewer sanitizing emitters may be used relative to a filter cartridge without a reflective chamber 522, thereby reducing the number of emitters to maintain a level of effectiveness. For example, a sanitizing emitter 506 including a single emitting element 318 may be used. In implementations where an emitting element 318 is a UV-LED, with a reflective chamber 522, battery life of the emitter source 200 may be extended relative to a filter cartridge without a reflective chamber 522.

The assembled filter cartridge 300 or 500 may be attached to the impermeable membrane 102. For example, the attachment mechanism 312 associated with the cartridge housing 310 and the complementary attachment mechanism 120 associated with the impermeable membrane 102 may be connected to one another. A seal may be formed between the filter cartridge 300 and the impermeable membrane 102 to prevent damaging agents from bypassing the filter cartridge 300. The sanitizing agent source 200 may be connected to the filter cartridge 300 to supply the sanitizing agent, such as by a wire of conduit. The user may activate the sanitizing agent source 200 to begin the supply of sanitizing agent to the filter cartridge 300. The source 200 may be activated by an actuator such as a switch, valve, or the like.

The user may put on the protective mask 100 by placing the impermeable membrane 102 over her face. For instance, the user may align the mouth and nose cover portion 114 with her nose and mouth and the eye cover portion 112, if included, with her eyes. The user may place the attachment member 104 around her head and/or neck and tighten the attachment member 104 to form a seal between the sealing element 118 and her face.

As the user breathes in, air is drawn into the filter cartridge 300, 500. The seal between the user's face and the impermeable membrane 102 formed by the 118 may prevent air from bypassing the filter cartridge 300. Thus, all the air the user breathes in or out passes through the filter cartridge 300. Damaging agents in the air may become trapped by the filter element 304 and may be deactivated by the sanitizing agent. Thus, if the damaging agent contacts the user, the user may not be harmed. Additionally, the sanitizing agent may keep the filter element 304 clean and prevent a buildup of damaging agents.

For example, if a user wearing the protective mask 100 is in an environment where airborne droplets of the SARS-CoV-2 virus are present, droplets drawn into the filter element 304 may become trapped or blocked by the filter element 304. UV light emitted by a sanitizing emitter 306 may deactivate the virus particles in the droplets by damaging the RNA. Droplets that might pass through the filter element 304 may be rendered non-damaging as the UV light deactivates the virus particles. As the user breathes in and out, the breath may be sanitized of virus particles, thus protecting the user and others.

The user may replace the filter cartridge 300 after a certain time, volume of air breathed, number of breaths, or if the filter element 304 becomes clogged. As the sanitizing agent source 200 becomes depleted, the user may replenish the sanitizing agent source 200. For example, the user may replace or recharge batteries, or replenish a reservoir or container of a sanitizing agent, thus maintaining the protection afforded by the protective mask 100.

Figure 13A:
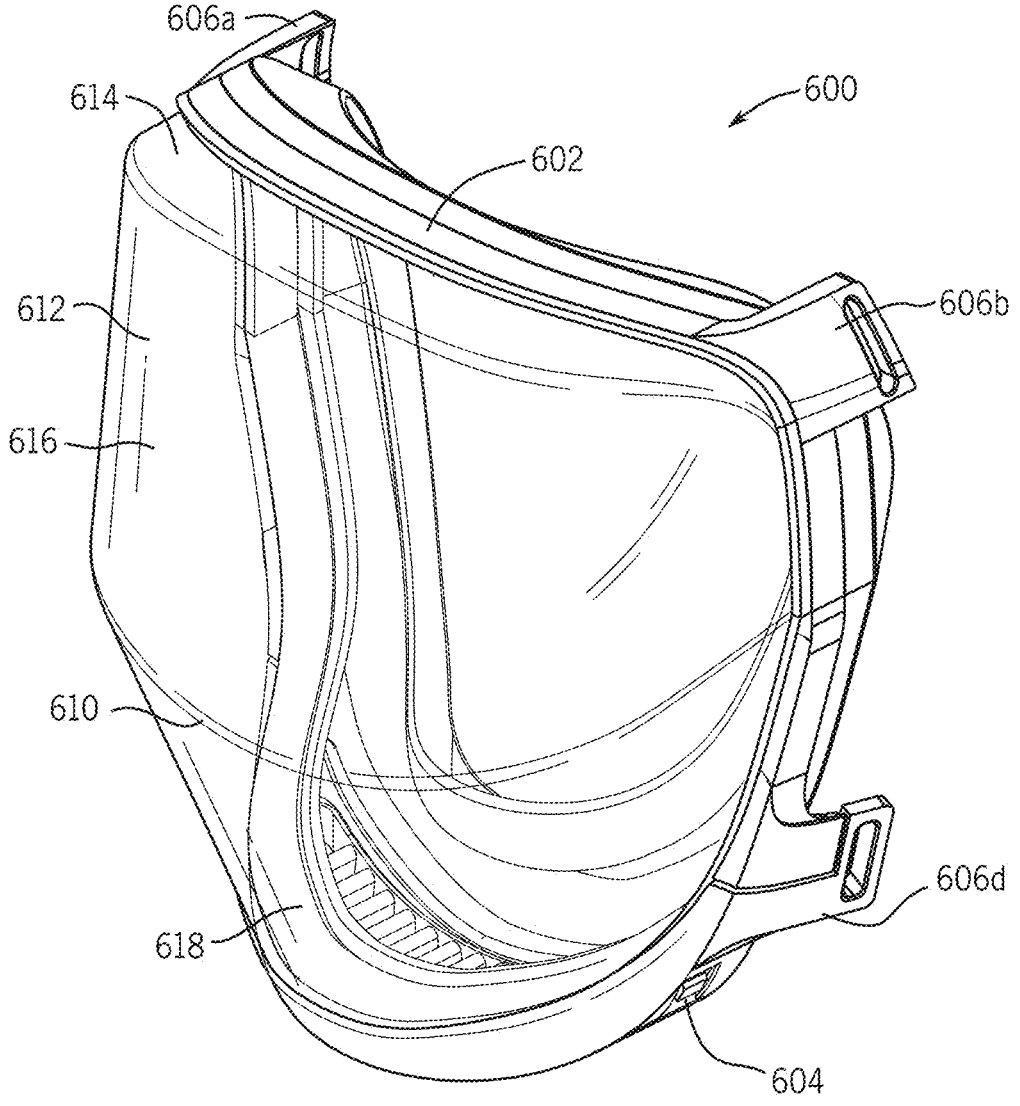
FIG. 13A is a front isometric view of a mask.
Figure 13B:
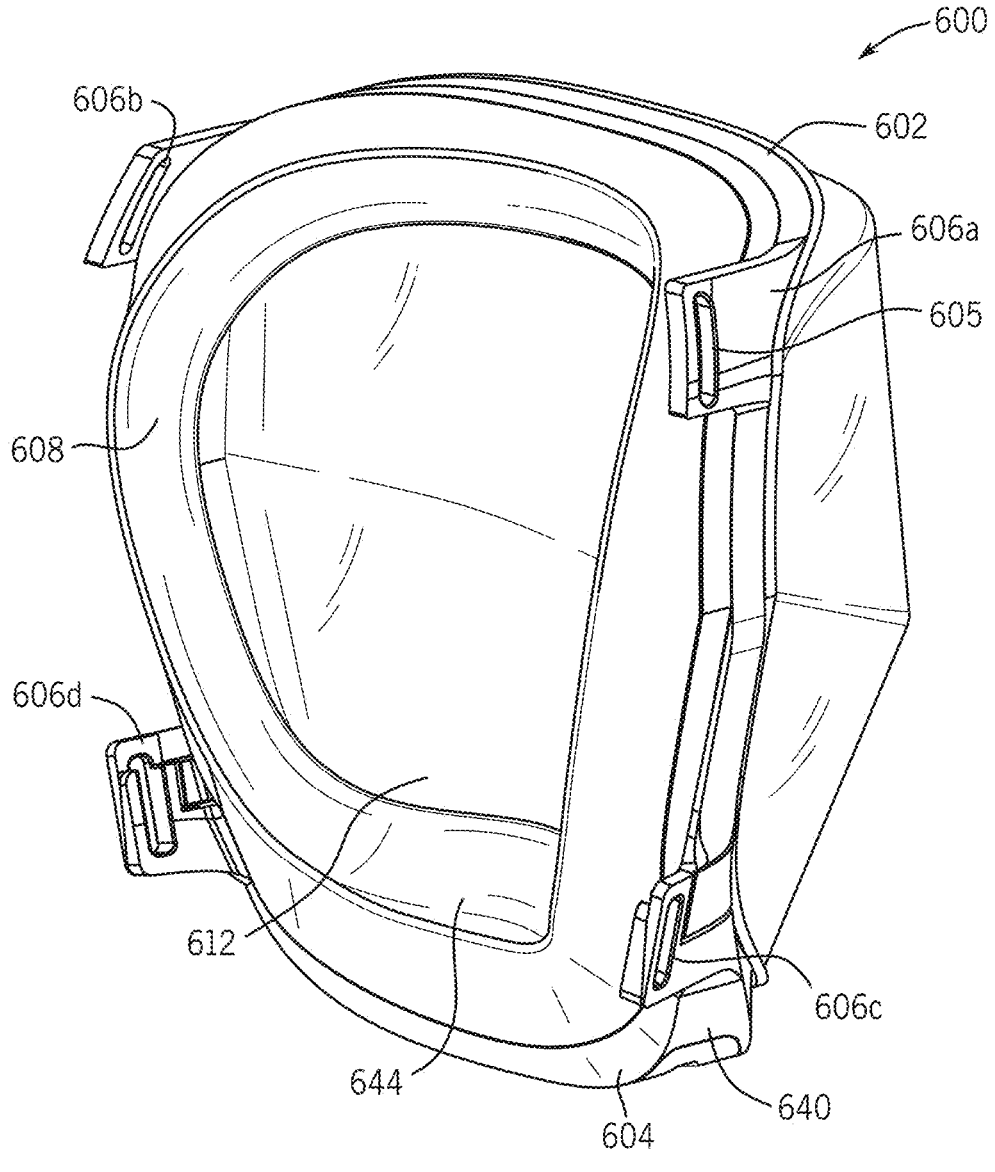
FIG. 13B is a rear isometric view of a mask.

FIGS. 13A and 13B illustrate another example of the mask 600. The mask 600 may be substantially similar to the mask 100 and other mask examples described herein. However, the mask 600 may include a frame that surrounds the face shield or lens, where the seal may be coupled to the frame and extend around a perimeter thereof and the filter cartridge may be coupled to the frame as well. In these examples, the mask 600 may have a larger transparent area allowing easier communication and visibility both to wearers of the mask and others interacting with the wearer (e.g., patients). Additionally, as shown in FIGS. 17A-17G and 18A-18G, the mask 600 may be formed of clear and/or transparent materials to allow the mask to be as "invisible" or unnoticeable as possible when worn on a user. FIGS. 17A-17G illustrate photographs showing the clear or transparent aspects of the mask 600 which are shown in line drawings in FIGS. 18A-18G of a mask 700. For example, various materials, such as the padding, seal, frame, and the like may be formed of clear or transparent materials.

The mask 600 and/or mask 700 may include an impermeable membrane 612, which may be substantially similar to the impermeable membrane 102. In some instances, the impermeable membrane 612 may be fully transparent or at least partially transparent and function as a lens or other viewable element to allow the user's facial features and expressions to be visible to others. The impermeable membrane 612 may be configured to extend away from the user's face, which may increase comfort for the user, as well as help to reduce fog from the user's breath. In one example, the impermeable membrane 612 may have a first or top portion 616 that extends downward from a top edge 614 at a first angle. The first portion 616 may transition at an inflection point 610 to a second portion 618, which may continue towards to a bottom edge at a second angle, different from the first angle. In this manner, the inflection point 610 may define a ridge or other boundary between the two portions 616, 618. It should be noted that the position of the inflection point 610 may vary across the surface of the impermeable membrane 612, such that the areas of the first and second portions 616, 618 may vary across the width of the impermeable membrane 612. In some embodiments, a center of the inflection point 610 is positioned to be adjacent to or align with the wearer's nose, such that the mask may define an increased volume or spacing between the user's face and the interior surface of the impermeable membrane 612 at a location corresponding to the user's nose. In other words, the impermeable membrane 612 may be configured to extend outwards to accommodate a user's nose, such that the nose does not impact or touch the interior surface of the impermeable membrane 612.

Figure 17A:
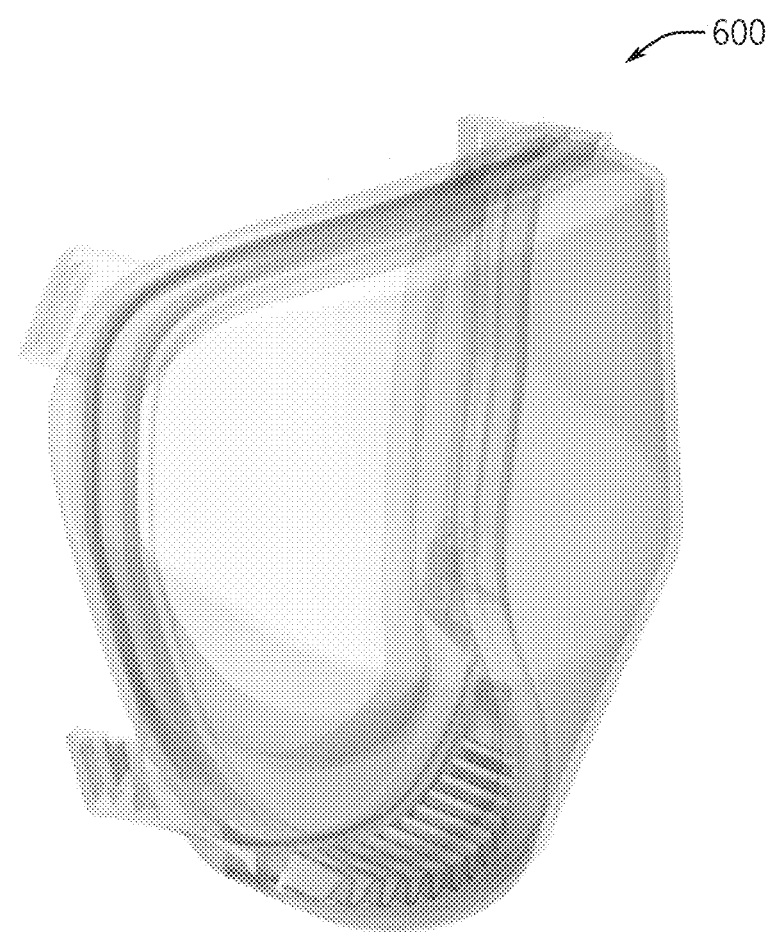
FIG. 17A is a front isometric view of a transparent mask.
Figure 17B:
FIG. 17B is a rear isometric view of the mask of FIG. 17A.
Figure 17C:
FIG. 17C is a front view of the mask of FIG. 17A.
Figure 17D:
FIG. 17D is a rear view of the mask of FIG. 17A.
Figure 17E:
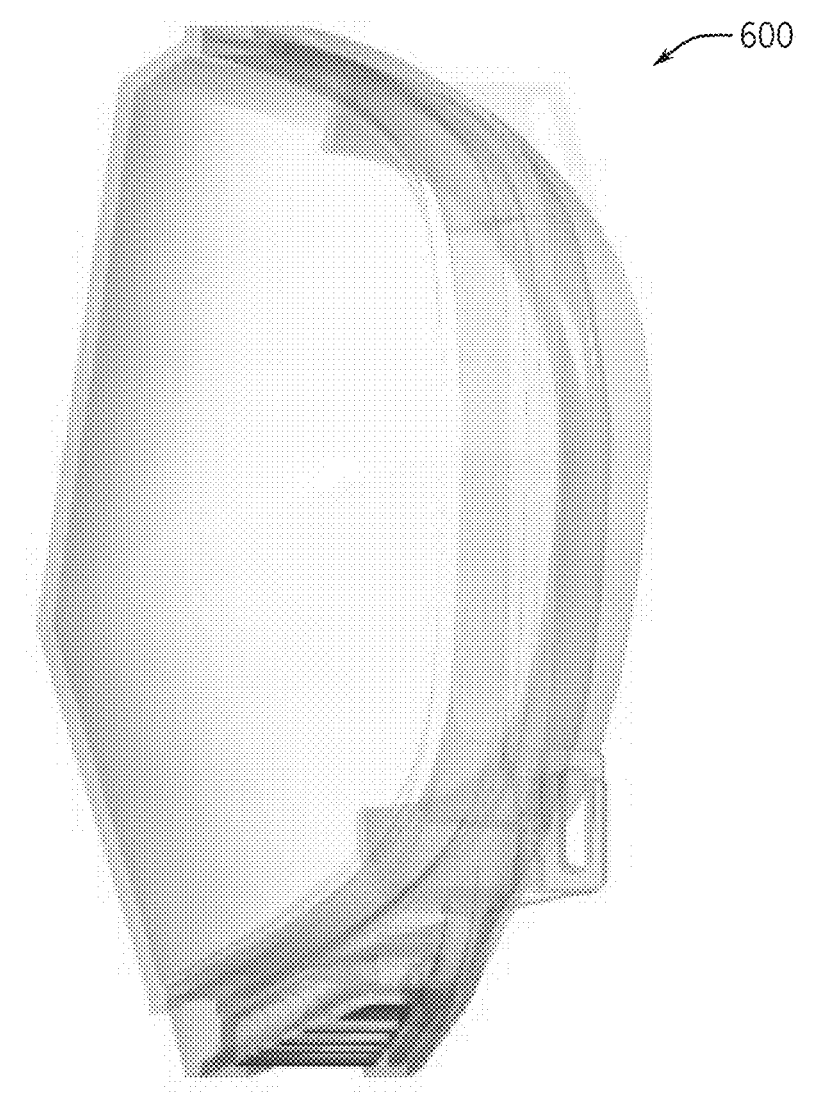
FIG. 17E is a side elevation of the mask of FIG. 17A.
Figure 17F:
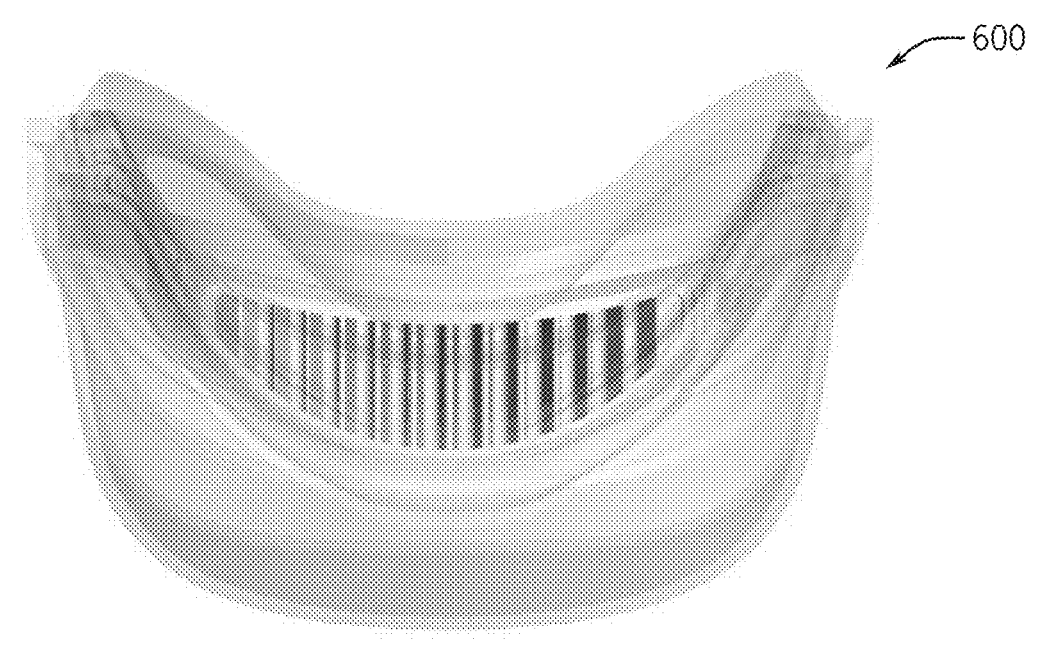
FIG. 17F is a top plan view of the mask of FIG. 17A.
Figure 17G:
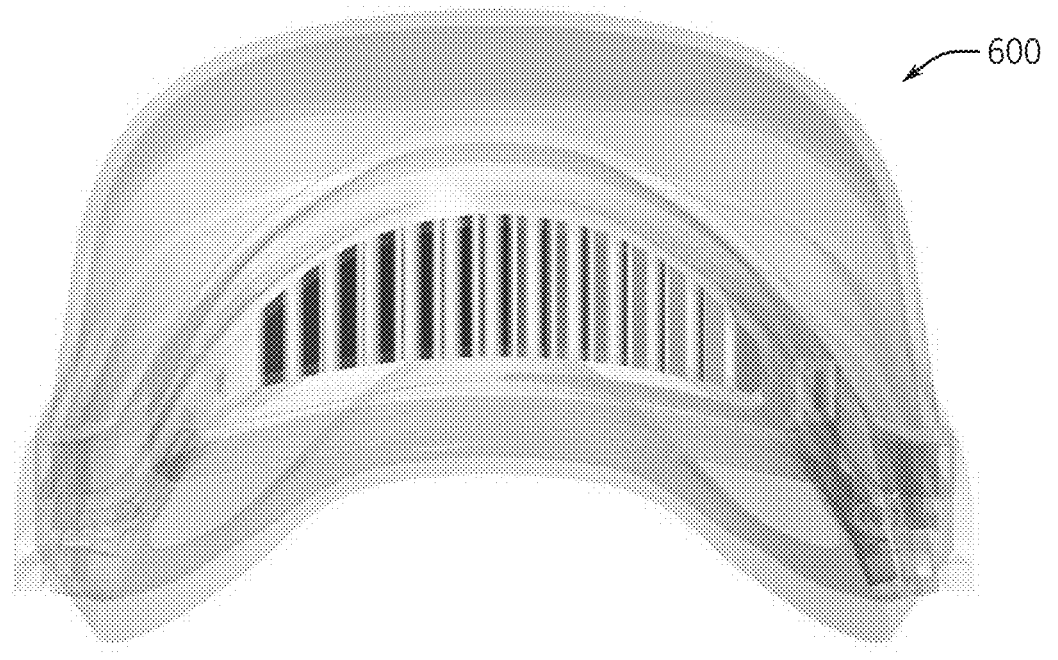
FIG. 17G is a bottom plan view of the mask of FIG. 17A.
Figure 18A:
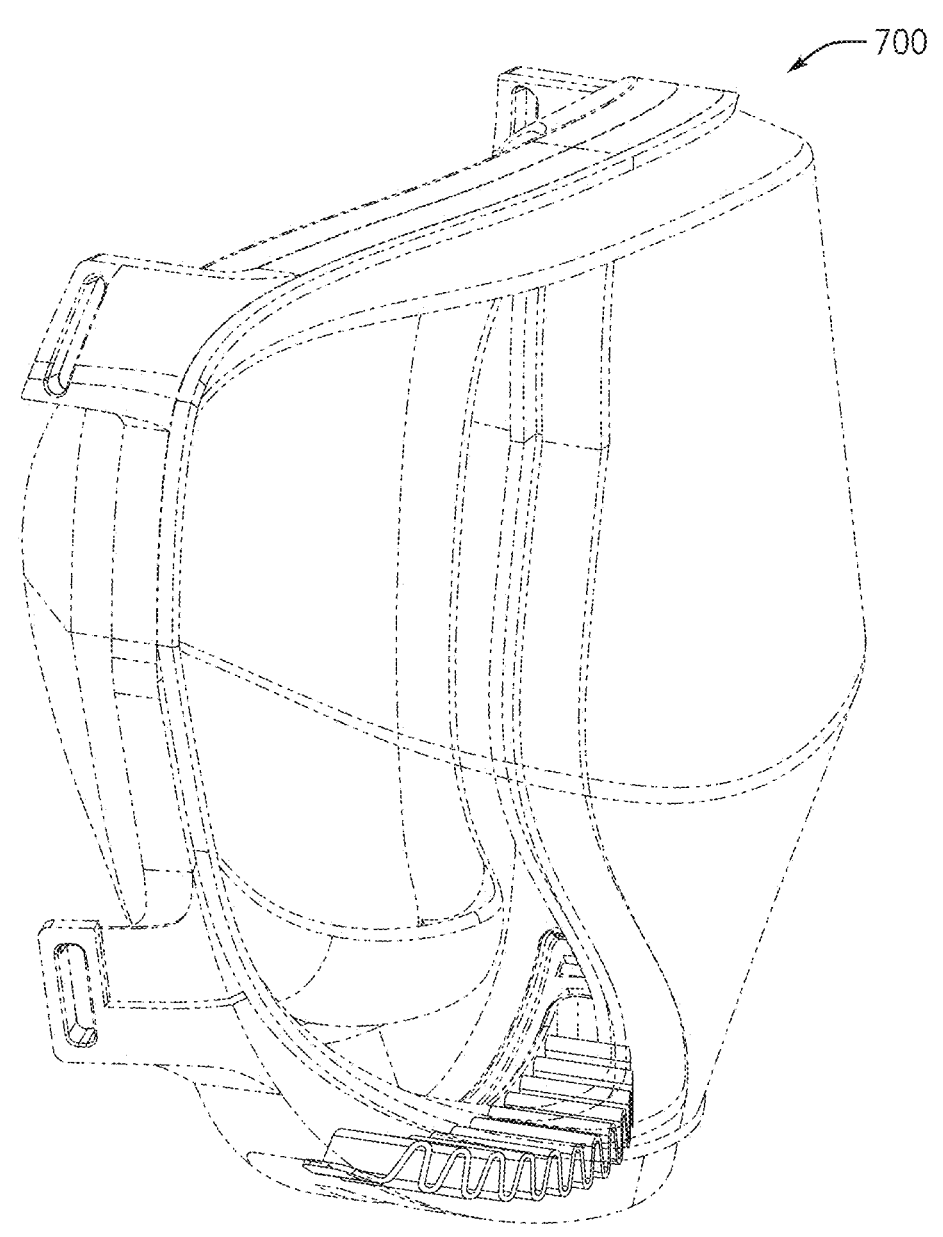
FIG. 18A is a front isometric view of a transparent mask.
Figure 18B:
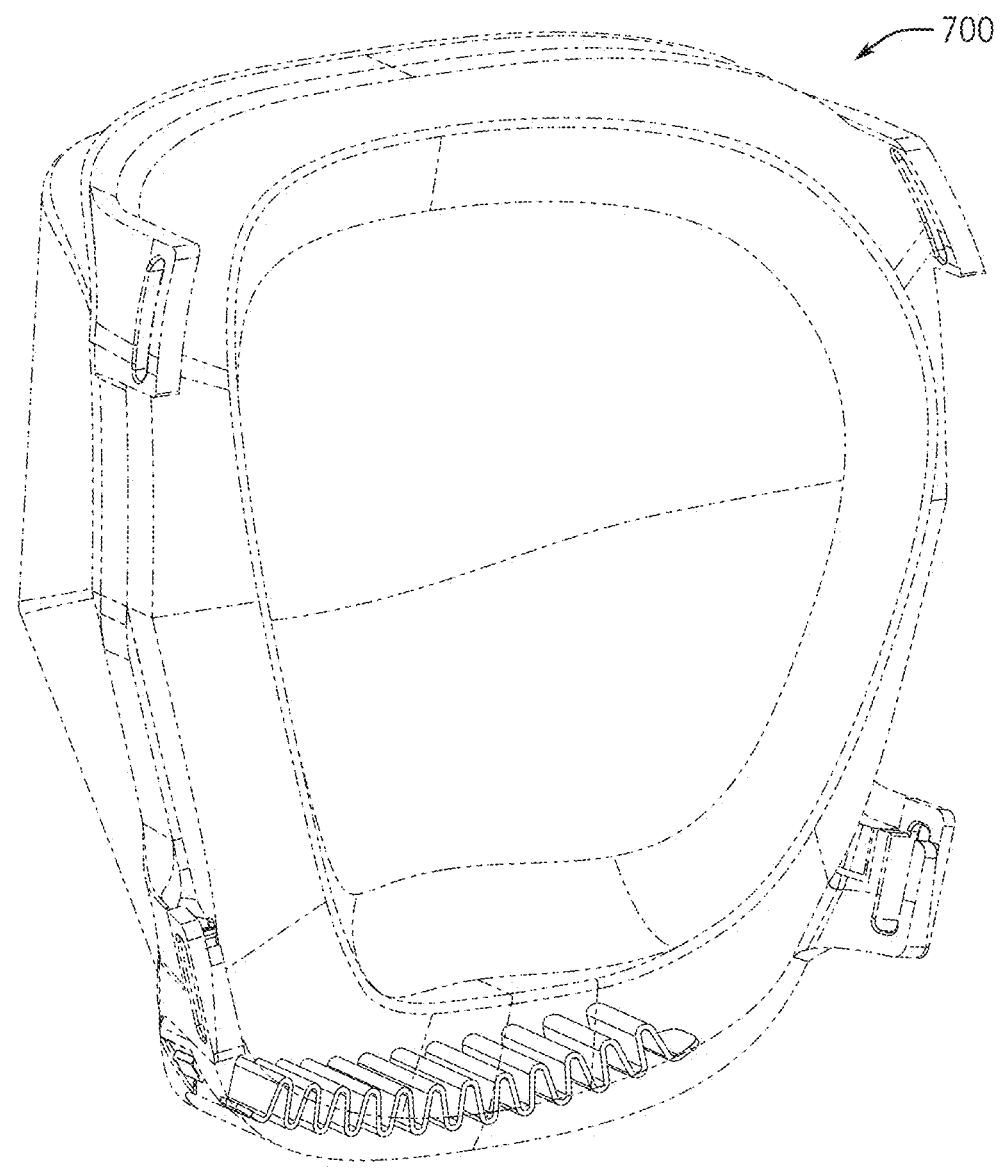
FIG. 18B is a rear isometric view of the mask of FIG. 18A.
Figure 18C:
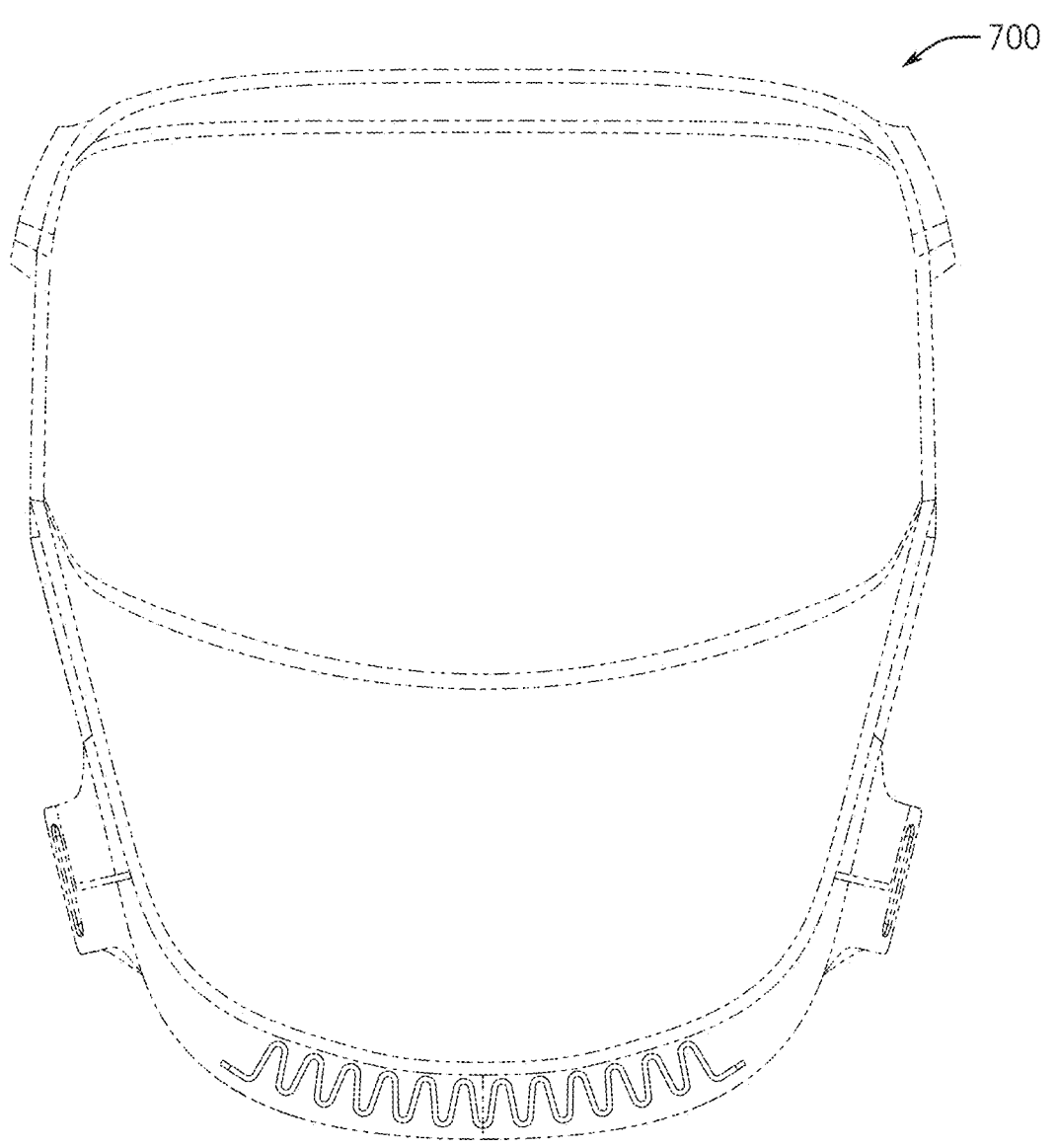
FIG. 18C is a front view of the mask of FIG. 18A.
Figure 18D:
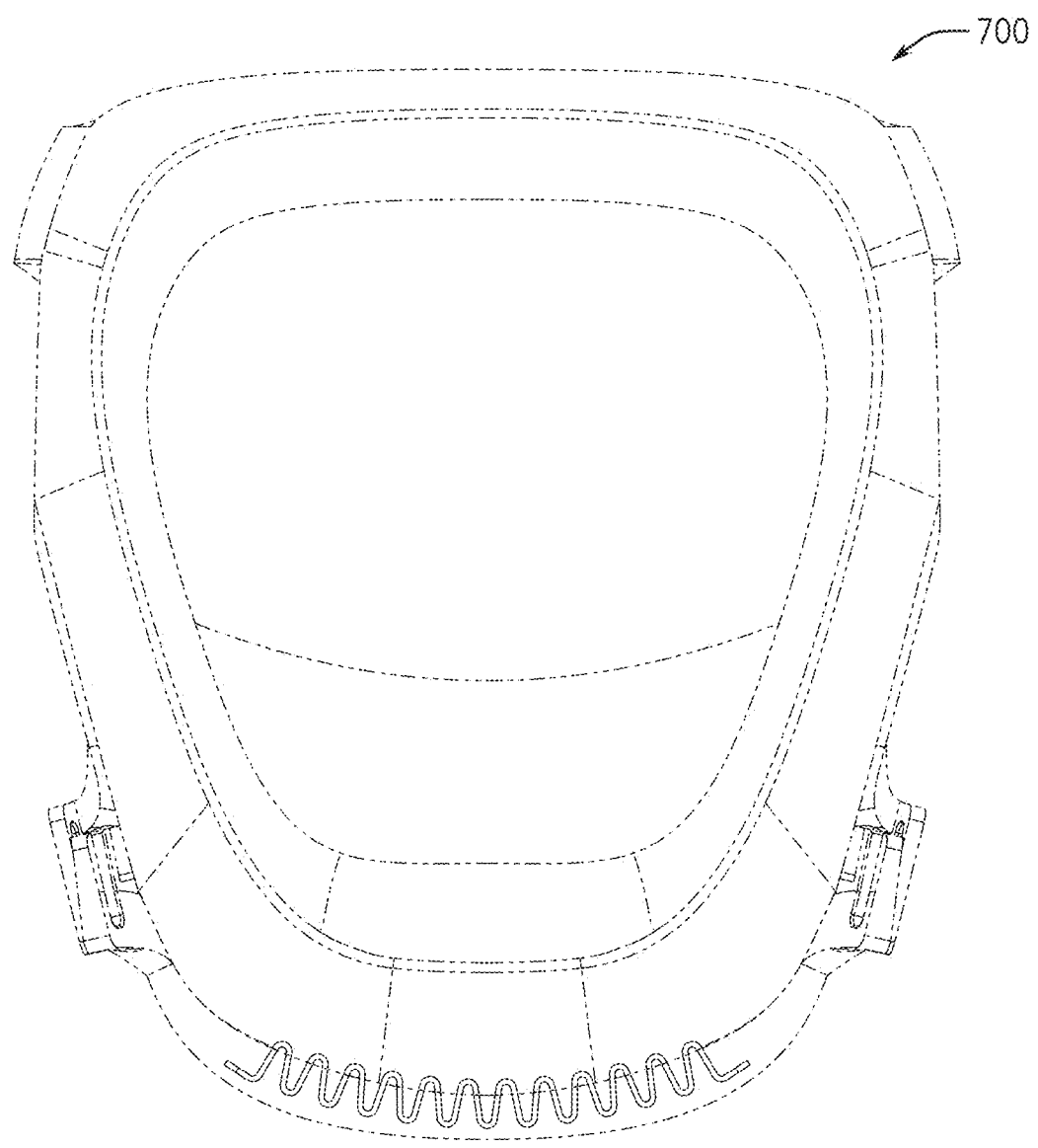
FIG. 18D is a rear view of the mask of FIG. 18A.
Figure 18E:
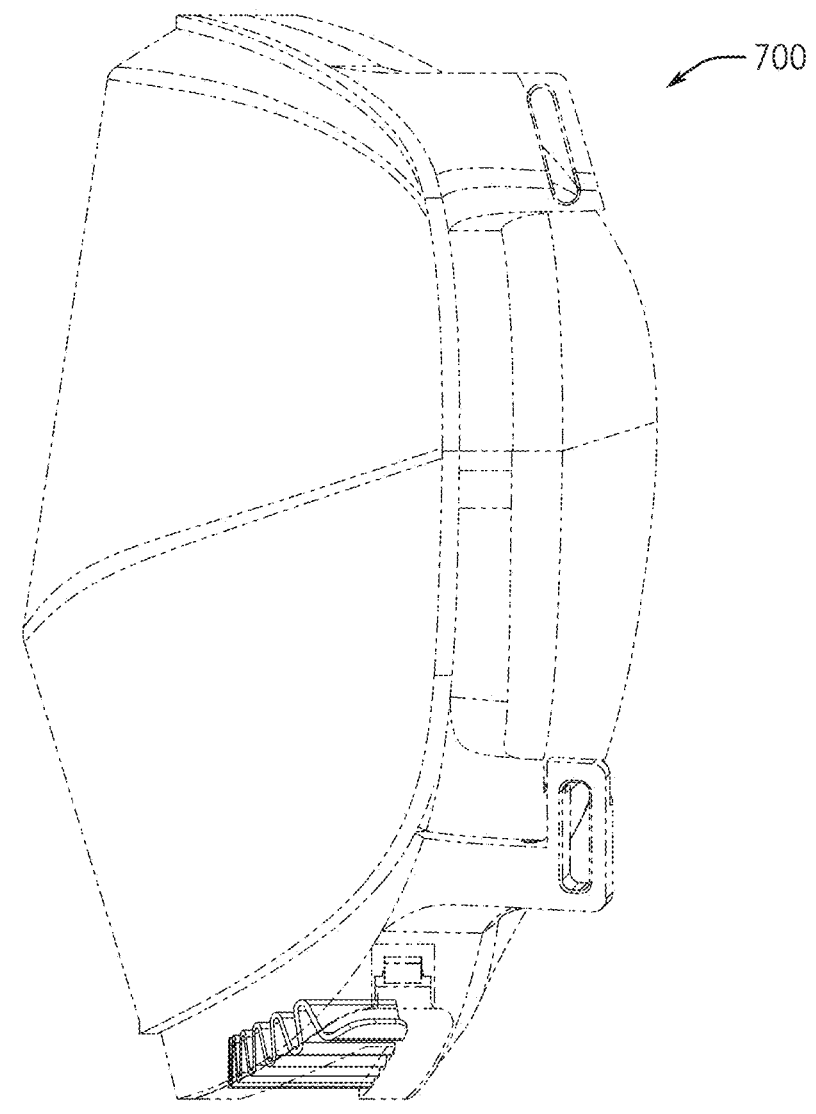
FIG. 18E is a side elevation of the mask of FIG. 18A.
Figures 18F, 18G:
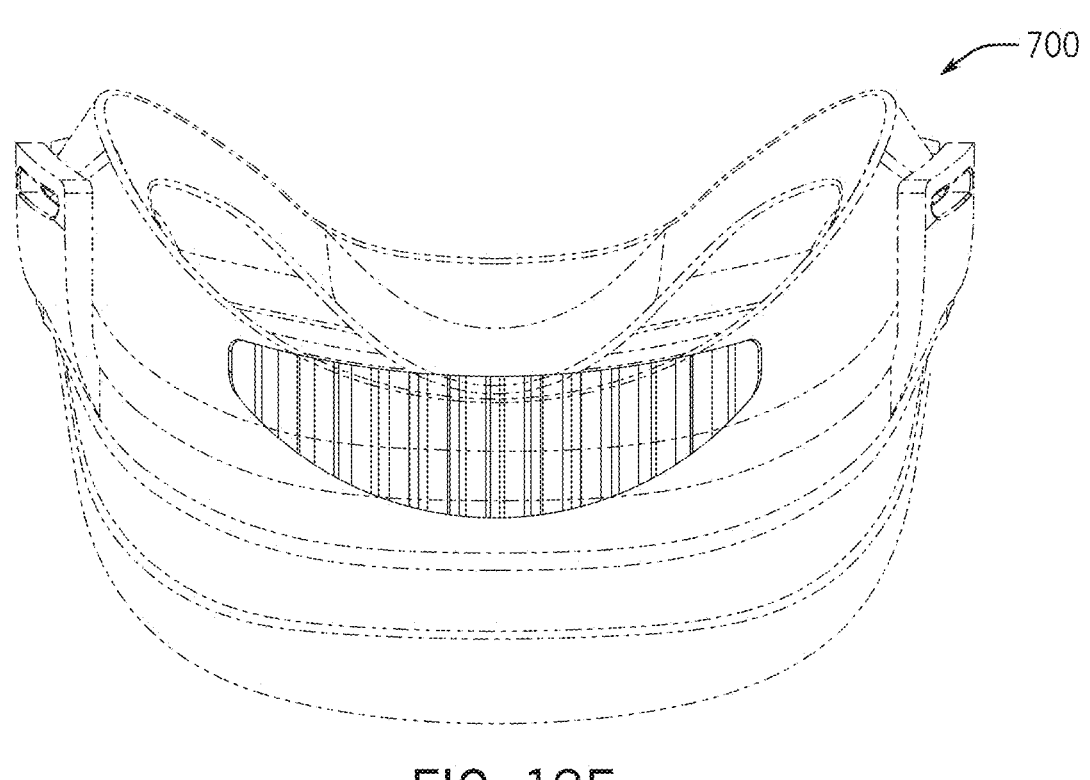
FIG. 18F is a top plan view of the mask of FIG. 18A.
FIG. 18G is a bottom plan view of the mask of FIG. 18A.

With reference to FIGS. 13B, 17B, and 18B, the mask 600 and/or mask 700 may include a frame 602 that couples to the impermeable membrane 612. The frame 602 may define a structural support for the mask 600 and/or 700 and may extend around a perimeter of the impermeable membrane 612. The frame 602 may include one or more securing supports 606a, 606b, 606c, 606d, which may be strap supports or strap connectors. In one example, the securing supports 606a, 606b, 606c, 606d may be formed as tabs that extend outwards and backwards from the frame 602 and that include strap apertures 605 for receiving a portion of a strap therethrough. In some embodiments, the mask 600 and/or 700 may be configured to be supported by two straps that extend around portion of a user's head and in these instances, there may be two sets of securing supports for each side of the mask 600 and/or 700 and for the top and bottom securing straps. The dual straps and positioning of the securing supports helps to distribute the force of the straps across multiple locations of the mask 600 and/or 700, making it more comfortable to wear.

The frame 602 may be formed of a rigid material, such as a plastic, and is configured to help define a seal for the mask 600 and/or 700 on the user's face. In some instances, the frame 602 may also house components, such as the filter cartridge. In these instances, the frame 602 may define one or more pockets that may receive the filter cartridge, batteries, or other components of the mask 600 and/or 700. In one embodiment, a cartridge pocket 642 may be defined on a bottom edge 640 of the frame 602, which positions the cartridge below the impermeable membrane 612, such that the user's mouth, nose, and eyes are not obscured by the cartridge when positioned on the frame 602. Relatedly, the frame 602 may include one or more securing features that may act to secure the cartridge to the frame 602. In some embodiments, the frame may be formed of a clear or substantially clear material.

A seal 608 extends around the interior of the frame 602 and is configured to be positioned on a user's face. The seal 608 may be a flexible material to conform to the user's face in order to prevent ingress of air and damaging agents between the user's skin and the bottom or exterior surface of the seal 608. In one example, the seal 608 may extend around the perimeter of the mask 600 and/or 700 and may have a curvature that corresponds with the user's facial features, e.g., may generally track the shape of the wearer's face. The seal 608 may be formed of an impermeable or substantially impermeable material, such as rubber, silicone, or the like. The seal 608 may include a bottom extension 644 or chin portion. The bottom extension 644 extends inwards towards the interior surface of the impermeable membrane 612 and defines an extended surface area for the seal 608. The bottom extension 644 is configured to seal against a user's chin and surrounding area, to assist in maintaining a seal as the user may move his or her mouth, e.g., while speaking. This extension 644 may act as a chin strap or chin seal. The seal may be formed as padding and include a soft feel to the user. In some embodiments, the seal may be formed of a clear or transparent material, such as clear silicone, rubber, or soft plastic. See, for example, FIGS. 17A-17G and 18A-18G showing the clear or transparent aspects of the seal.

Figure 16:
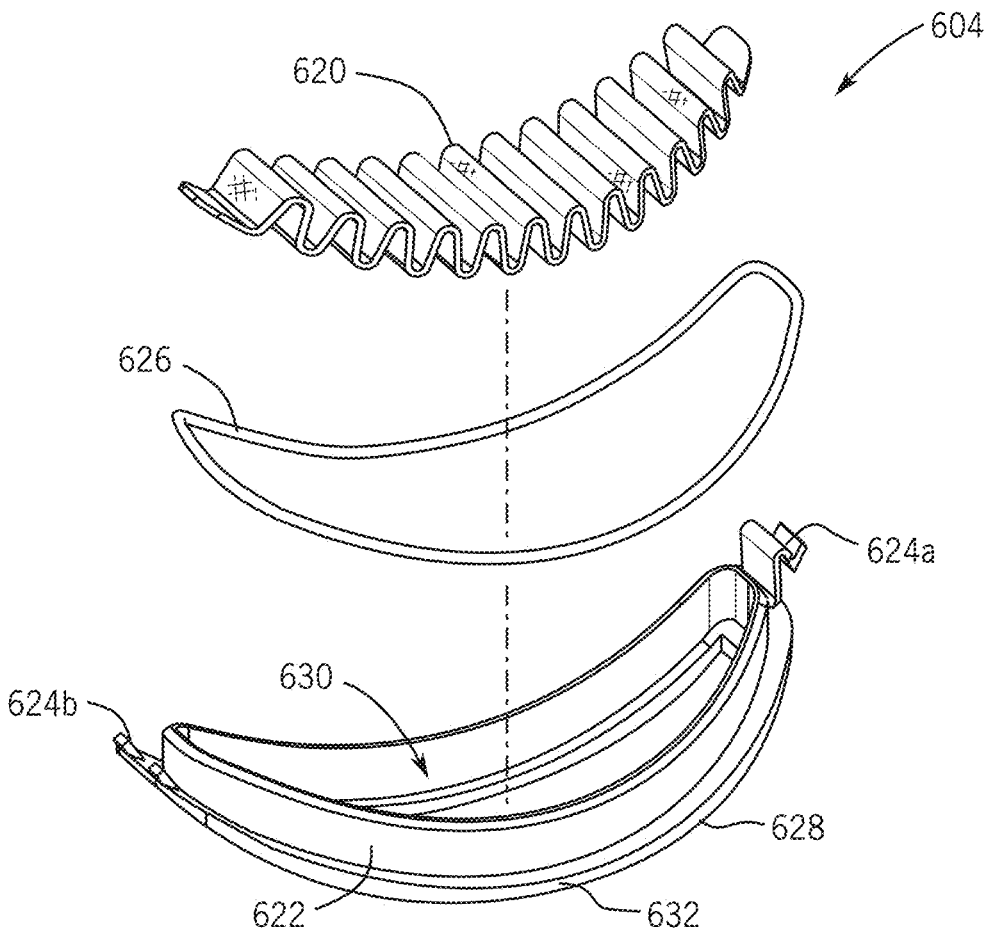
FIG. 16 is an exploded view of a filter cartridge.

FIG. 16 illustrates an exploded view of the filter cartridge 604. The filter cartridge 604 may be configured to be movable so as to be accessed by a user to replace a filter 620 positioned therein. For example, the filter cartridge 604 may be pivotable, removable, or rotatable relative to the frame 602. In one example, the filter cartridge 604 may define a pocket 630 or cavity for receiving the filter. As one example, the filter cartridge 604 may define a cartridge body 628 that may have a curvature matching the frame 602 at the connection location, such that the cartridge 604 may seat within the frame 602. The cartridge body 628 may be shaped as an oval with a curvature along its length, e.g., a middle portion of the cartridge body 628 may be positioned in a lower plane than the two ends of the cartridge body 628. The curvature may be selected to also correspond to a shape of the user's face, e.g., the lower most portion of the cartridge body 628 may be aligned with a user's chin when positioned on the user's face.

A lip 622 may extend upwards from a top surface of the cartridge body 628 and extend around the perimeter of the of the cartridge body 628. In one embodiment, the lip 622 is inset from an outer edge of the cartridge body 628, such that a shelf 632 or ledge is defined between the outer edge of the cartridge body 628 and the outer edge surface of the lip 622.

Coupling features 624a, 624b may be coupled to the cartridge body 628. The coupling features 624a, 624b allow the cartridge 604 to be movable or detachable from the frame 602. In one example, the coupling features 624a, 624b may be formed as mechanical components that couple to corresponding features within the frame 602. As one example, a first coupling feature 624a may be formed as a flexible tab that may flex and spring back to an original configuration. As another example, a second coupling features 624b may be formed as two prongs that extend outwards away from the cartridge body 628. However, other coupling features 624a, 624b may be used as well, e.g., hinges, fasteners, or the like.

A gasket 626 may be positioned on the cartridge body 628 to assist in sealing the cartridge body 628 to the frame 602. The gasket 626 or seal may be formed of a compressible material that compresses and expands to fill the connection between two components. In one example, the gasket 626 is positioned on the shelf 632 and is positioned against the exterior surface wall of the lip 622.

A filter 620 is coupled to the cartridge body 628. For example, the filter 620 may be positioned within the pocket 630 and expand against an interior surface of the lip 622. The filter 620 is configured to fill the entire pocket 630, such that any air flow through the cartridge 604 must be through the filter 620. The filter 620 may be held in a position via friction fit (e.g., the filter 620 may be slightly larger than the pocket and compress to be held in position), adhesive, fasteners, or the like. In some examples, the filter 620 may be removable from the cartridge 604, allowing a user to remove the filter 620 and replace it as needed or desired. In other examples, the entire cartridge 604 may be configured to be removed and replaced as needed. The filter 620 is generally a filtering material, such as fabric, synthetic plastic fibers, fiberglass, (woven or non-woven) that is configured to allow molecules of a particular size therethrough, e.g., limit the size of molecules that can flow through. In some examples, the filter 620 may be a fine mesh of synthetic polymer fibers, such as a nonwoven polypropylene fabric that may filter 95% of airborne particle. The filter 620 may also have a minimum efficiency reporting value (MERV) rating of 13 to 16, and preferably 16, to capture particles greater than 0.3 micrometers, where the particles that are captured including bacteria, droplets, and the like. The filter 620 may also be pleated or otherwise be folded in order to increase the surface area within the cartridge 604.

To assemble the mask 600 and/or 700, the impermeable membrane 612 may be coupled to the frame 602. For example, the impermeable membrane 612 may be secured via molding, adhesive, ultrasonic welding, or the like. The seal 608 may be secured to the frame 602 in similar manners and be positioned so as to form a bottom engagement surface of the mask 600 and/or 700 and be inwardly inset from an exterior edge of the frame 602. Straps 648a, 648b may be coupled to the frame 602 via the securing supports 606a, 606b, 606c, 606d. For example, a first or top strap may be threaded through securing supports 606a, 606n and a second or bottom strap may be threaded through securing supports 606c, 606d.

The filter cartridge 604 may be received within the cartridge pocket 642 and secured in position. For example, coupling components 624a, 624b may be received within corresponding features on the frame 602 adjacent to or formed within the walls defining the cartridge pocket 642. The coupling components 624a, 624b may be configured, such as that a first end of the cartridge 604 may remain attached to the frame 602, which the second end may be detached, such that the cartridge 604 can pivot relative to the frame 602, which may allow a user to open or pivot the cartridge in order to access and replace the filter 620. When secured in position on the frame 602, the gasket 626 compresses in position and then expands to engage the walls of the frame 602. In this manner, the gasket 626 or seal prevents flow of damaging agents and/or air through the frame 602 and all air flow is through the filter 620.

Figures 14A, 14B, 14C:
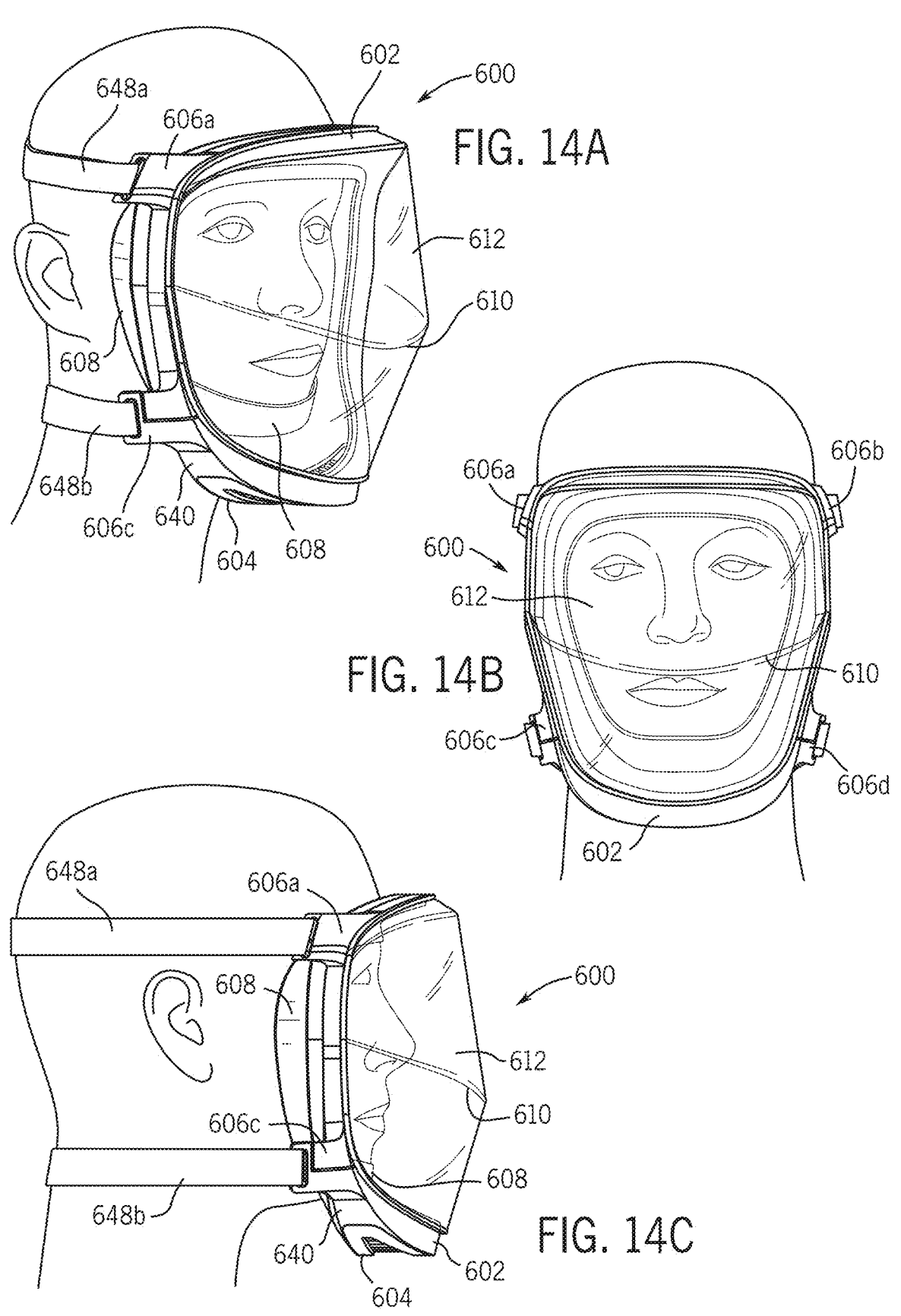
FIG. 14A is a front isometric view of a mask as worn by a user.
FIG. 14B is a front elevation view of the mask of FIG. 14A.
FIG. 14C is a side elevation view of the mask of FIG. 14A.
Figure 15:
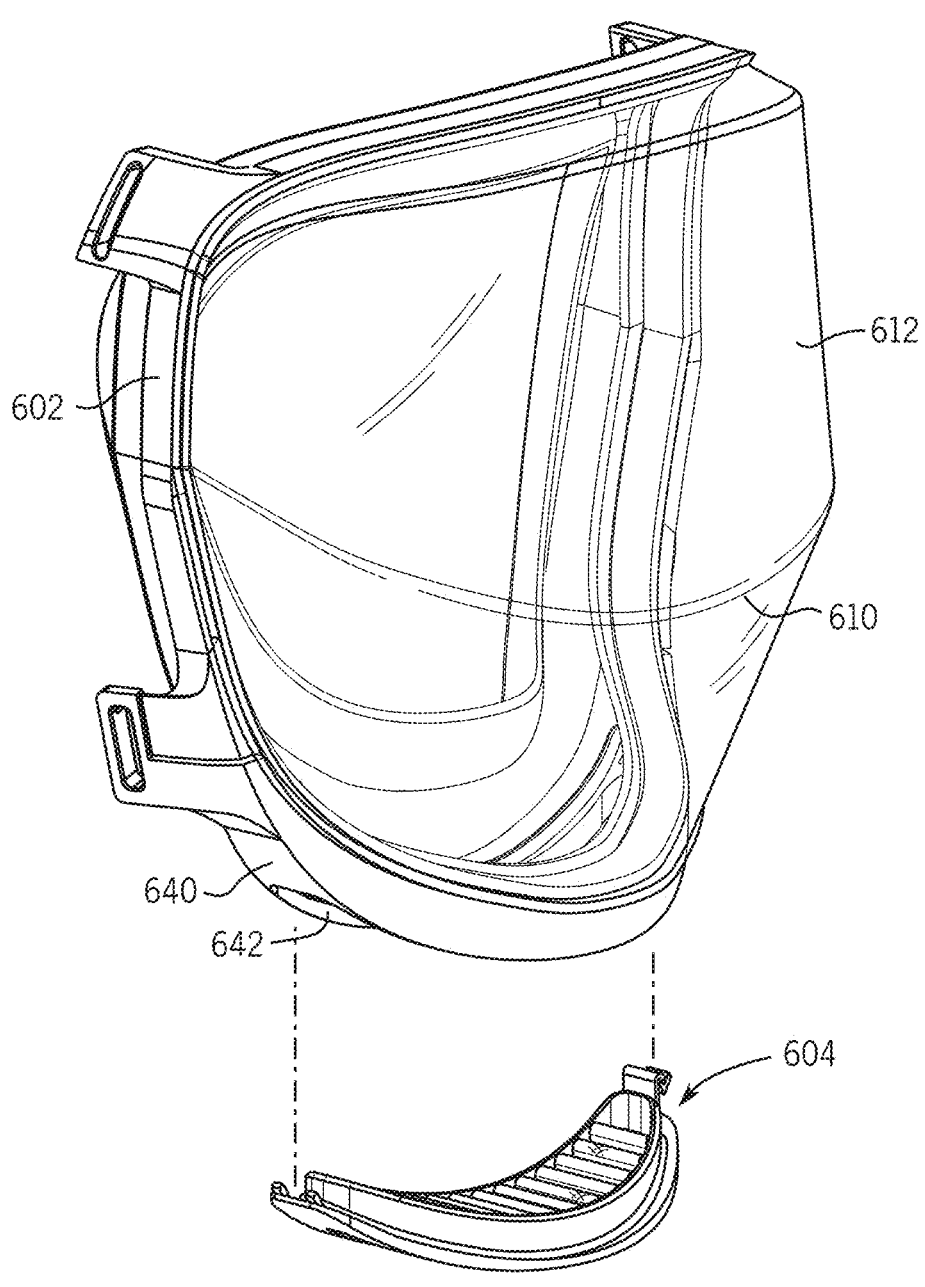
FIG. 15 is an exploded view of the mask of FIG. 13A.

With reference to FIGS. 14A-14C, to use the mask 600 and/or 700, the user may position the mask 600 on his or her face, that the top end of the mask 600 is positioned adjacent his or her forehead and a bottom end of the mask 600 is positioned adjacent his or her chin. The straps 648a, 648b may be positioned around the user's head, above and below the ears, respectively. The seal 608 then engages the user's face, sealing against the user's skin and conforming to the shape of the user's face. Air can flow into and out of the space defined between the user's face and the impermeable membrane 612 via the cartridge 604. The cartridge 604 acts to filter the air flow, such that particles, droplets, and the like, that are above a predetermined size cannot flow either into or out of the filter 620. In this manner, the user is protected from air flow with damaging agents and others are protected from any damaging agents breathed out by the wearer. Because the frame 602 and seal 608 may extend around the user's eyes, mouth, and nose, the user's facial expressions can be more easily seen by others when the impermeable membrane 612 is transparent. This allows emotions to more readily conveyed to others, as well as assists in communication between others.

FIGS. 19A-19F illustrate another example of a mask 800. The mask 800 may be substantially similar to the mask 100, the mask 600, and other mask examples described herein. Like the mask 600, the mask 800 may include a frame that surrounds the face shield or lens. The seal may be coupled to the frame and extend around a perimeter thereof. The filter cartridge may be coupled to the frame as well. The mask 800 may have a transparent area sufficiently large to allow visibility of the user's face to others with whom the user interacts (e.g., patients). The transparent area may be sufficiently large so as to not obstruct the user's peripheral vision.

The mask 800 may include an impermeable membrane substantially similar to the impermeable membranes 102 and 612. In some instances, the impermeable membrane 812 may be fully transparent or at least partially transparent. In some examples, the impermeable membrane 812 may function as a lens to other viewable element to allow the user's facial features and expressions to be visible to others. The impermeable membrane 812 may be configured to extend away from the user's face. Such an arrangement may increase user comfort and may help reduce fogging of the impermeable membrane 812, such as due to the user's breath, perspiration, or the like. In some embodiments, the lens 812 may be configured to define an extra pocket or space adjacent to a user's mouth and nose, allowing a more comfortable fit and helping to reduce fogging.

In some examples, the impermeable membrane 812 includes a first portion 816 or top portion that curves around or corresponds to the user's face. The first portion 816 may extend approximately from the user's forehead to the user's chin, when the mask 800 is in use. Such a large first portion 816 may be beneficial to place an inflection line or point out of the user's line of sight. The first portion 816 may extend away from the user's face such that the user's face does not contact the impermeable membrane 812. The first portion 816 may transition to one or more second portions 817 at an inflection line 810. The second portions 817 may be disposed on respective left and right sides of the first portion. The second portions 817 may be planar or may be curved. The first and second portions may transition to one or more third portions 819. The third portion 819 may extend across the user's chin between left and right second portions. The third portion 819 may be curved or may be planar. The impermeable membrane 812 may include a rim 815 configured to be received in a portion of a frame 801 of the mask 800

In some embodiments of the mask 800, the impermeable membrane 812 is received in a frame 801. The frame 801 may include a first frame portion 802 and a second frame portion 803. The frame portions 802 and 803 may interlock with one another and/or with other components of the mask 800 to provide a stable platform for the impermeable membrane 812 and to secure the mask 800 to a user's face. For example, the first frame portion 802 and the second frame portion 803 may be coupled to one another at a joint 805 (see, e.g., FIG. 19B). In some embodiments, two joints 805 are disposed at respective left and right sides of the mask 800. In some embodiments, the first frame portion 802 is an upper frame portion and the second frame portion 803 is a lower frame portion. The joined frame portions 802 and 803 forming the frame 801 may extend around the perimeter of a user's face. The frame 801 may be formed of similar materials to the frame 603, for example a rigid material like plastic. Using a rigid material may help seal the mask 800 to the user's face, such as with a seal 808.

Either or both of the upper frame portion 802 and/or the lower frame portion 803 may include one or more securing supports 806 such as securing supports 806_a_, 806_b_, 806_c_, and/or 806_d_. The securing supports 806 may be substantially similar to the securing supports 606 (e.g., securing supports 606_a_, 606_b_, 606_c_, 606_d_) described herein, further description of which is omitted for the sake of brevity.

The frame 801 may receive other components of the mask 800 such as a seal 808, a filter cartridge 804, a sanitizing agent source such as batteries 200, a brace 823, a sanitizing agent source cover 821, a cartridge receptacle 820, and/or one or more straps (e.g., received in the securing supports 806).

For example, the upper frame portion 802 may receive the brace 823 in an upper portion thereof. The brace 823 may form a portion of a sanitizing agent compartment, such as a compartment that houses one or more batteries 200 or other power source. The brace 823 and/or a portion of the upper frame portion 802 may receive or selectively couple to the sanitizing agent source cover 821 such as to enclose one or more sanitizing agent sources such as one or more batteries 200 in the mask 800.

The seal 808 may be received in the frame 801. The seal 808 may be substantially similar in many aspects to the seal 608, which are not repeated, for the sake of brevity. For example, the seal 808 may be formed of a flexible or deformable material to conform to and seal against the user's face in order to prevent or reduce ingress of air and damaging agents between the user's skin and the bottom or exterior surface of the seal 808. The seal 808 may include a chin portion or bottom extension 809 similar to the bottom extension 644 (shown for example in FIG. 19D) that seals against the user's chin and possibly a portion of the user's neck to provide an effective seal against the ingress of air and/or damaging agents between the user's face and the mask 800.

The cartridge receptacle 820 may couple to, or be received in, a portion of the frame 801. For example, the cartridge receptacle 820 may couple to the lower frame portion 803. The cartridge receptacle 820 may be formed of a rigid material such as plastic or metal and configures to receive a filter cartridge 804. The cartridge receptacle 820 may provide a sturdy foundation for the filter cartridge, such that the interface between the receptacle and the cartridge is resistant to bending, torsion, or other flexure and the formation of gaps that may create a passage around the filter cartridge 804 to the user's face. The cartridge receptacle 820 may act as a containment element that contains the sanitizing agent such as to protect the user from exposure to the sanitizing agent. For example, the cartridge receptacle 820 may block UV light emitted by the sanitizing emitter from the user's face. The cartridge receptacle may include one or more apertures that allow sanitized air to flow from the filter cartridge to the user's mouth.

The filter cartridge 804 may be similar to other filter cartridges disclosed herein and include a sanitizing emitter and a filter element such as to trap and/or neutralize damaging agents. The filter cartridge 804 may be removable attachable to the cartridge receptacle 820 and thus to the mask 800. The sanitizing emitter 826 may be formed of a circuit board 827. The circuit board 827 may be a rigid board (e.g., fiber reinforced board such as an FR4 board) or a flexible circuit board. The sanitizing emitter 826 includes one or more emitting elements 828 which may be operative to emit a sanitizing agent to neutralize a damaging agent, similar to other emitting elements described herein. In many embodiments, the emitting elements 828 are LEDs or more specifically LEDs that emit light in a UV spectrum. The one or more emitting elements 828 may be electrically coupled to the circuit board 827 so as to receive electrical power from the batteries 200 distributed by the circuit board 827. The one or more emitting elements 828 may be physically coupled to the circuit board 827 so as to support and position the sanitizing emitters relative to the filter element 836 such that the emitters may be disposed to permeate the filter element 83 with a sanitizing agent. The batteries 200 may supply power to the sanitizing emitter 826 and to the emitting elements 828 via one or more wires (not shown) that extend from batteries 200 received in the battery compartment through a portion of the frame 801, to the sanitizing emitter either directly, or via a controller 844.

The sanitizing emitter 826 may be disposed over, or received in a first gasket 830. The first gasket 830 may include a first gasket body 834. The first gasket body 834 may be a thin element with a recess to receive the sanitizing emitter 826. The first gasket body 834 may have one or more apertures 832 formed therein to enable air to pass through the body 834 into or out of the mask 800. The interstitial portions of the body 834 between the apertures 832 may form one or more ribs 833 operative to support the sanitizing emitter 826. The sanitizing emitter may be disposed so as to permeate the filter element 836 with a sanitizing agent operative to deactivate the damaging agent.

The filter element 836 may be similar to other filter elements disclosed herein. For example the filter element 836 may be suitable to trap a damaging element to prevent it from reaching the user. The filter element 836 may be planar, curved, or U or L-shaped. The filter element 836 may be formed of a woven or non-woven material. The filter element 836 may be replaceable, such as when soiled, clogged, or at the end of its useful life. The filter element 836 may be received in, or disposed over a portion of a second 838. The second gasket 838 may include a second gasket body 842. The second gasket body 842 may be a thin element with a recess to receive the filter element 836. The second gasket body 838 may have one or more apertures 840 formed therein to enable air to pass through the body 838 into or out of the mask 800. The aperture 840 may be a single aperture or may be multiple apertures, similar to the apertures 832 with ribs similar to the ribs 833.

The first gasket body 834 and/or second gasket body 838 may be planar, may be curved, may be in an L-shape (as shown for example, in FIG. 19E), may be a U-shape, or other shape. An advantage of a curved, L, U or similar shape may be the ability to include more surface area for the filter element 836 and/or sanitizing emitter 826 by wrapping a portion of the element back toward the user's face, such as to enable easier breathing and/or longer filter life. The first gasket 834 and the second gasket 838 may seal to the housing 822 and/or the cartridge receptacle 820 so as to reduce or prevent the bypass of air or a damaging agent around the sanitizing emitter 826 and/or filter element 836.

The filter cartridge 804 and the cartridge receptacle 820 may be adapted to snap, click, slide together, or otherwise be assembled without the use of tools, such as to make it easy for a user to insert and replace the filter. For example, the filter cartridge may include a housing 822 that receives other components of the filter cartridge such as a sanitizing emitter 826, a filter element 836, and one or more seals or gaskets. The housing 822 may include one or more rails 856 adapted to be received in a portion (e.g., a respective aperture) of the cartridge receptacle 820. The rails 856 may act as guides to align the filter cartridge 804 with the cartridge receptacle 820. The one or more rails 856 may be disposed in a portion of the housing 822 other than as shown.

The controller 844 may be received in, and/or coupled to, the cartridge receptacle 820. A controller cover 824 may be received over the controller 844 and coupled to the cartridge receptacle 820 to house or enclose the controller 844. The controller cover 824 may be selectively removable from the mask 800, e.g., to allow recharging, servicing, or replacement. The controller 844 may be operative to control and/or communicate the operation of the sanitizing emitter 826. The controller 844 may include on or more indicators 846 such as LEDs that indicate a status of the mask 800. For example, the indicators 846 may communicate battery charge status (e.g., charged, partially charged, depleted, or the like). In other examples, the indicators 846 may indicate the radiant power of the sanitizing emitter, a fault condition, or the like. The indicators 846 may change color, flash, or pulsate, to indicate status to a user. The indicators 846 may be visible to a user while wearing the mask 800 and/or may be visible to a person other than the user.

The controller 844 may include a first actuator such as a power actuator 848 with an operator interface 850 operative to turn the sanitizing emitter on/off and/or to adjust the radiant power of the sanitizing emitter. The power actuator 848 may be an on/off switch, tactile switch, a variable resistor, capacitive touch input, or the like. The controller 844 may include a second actuator 852 with an operator interface 854. The operator interface 854 may be received in an aperture 825 formed in the controller cover 824. The second actuator 852 may be operative to reset the operation of the mask 800, such as after a fault, when installing new batteries 200, and/or a new filter cartridge. Either of the operator interfaces 850 or 854 may be suitable to interface with the fingers and/or hands of a user, such as a button, slider, or the like.

In some implementations, a mask such as a mask 100, 600, or 800 may include one or more sensors that can detect the presence of the sanitizing agent. For example, a sensor may be disposed to detect leakage of the sanitizing agent from the filter cartridge. In some implementations, the sensor is a sensor adapted to detect UV light emitted by a sanitizing emitter 306, 506. The sensor may provide a warning to a user that the integrity of the mask is compromised. Additionally, the sensor may provide a warning to the user of sanitizing agents from sources outside the mask. In some implementations, a sensor may be disposed so as to detect proper operation of the mask. For example, a sensor may be disposed in a filter cartridge and may confirm that a sanitizing agent is being emitted. In some implementations, sensors may be disposed both to warn of leakage of the sanitizing agent and to confirm operation of the mask.

In some implementations, a mask 100, 600, or 800 may include an expansion interface. An expansion interface may enable the addition of other capabilities to a mask. For example, an expansion interface may be configured to accept a communications component such as a microphone. A communications component may enable a user to communicate with others while wearing the mask. A communications component may be in wired or wireless communication with another communications device such as a user's phone to enable a user to make phone calls while wearing a mask.

In some implementations, a portion of the impermeable membrane may be configured to display information projected therein. For example, a portion of the impermeable membrane may be adapted to form a portion of a heads-up display. A suitable projector may be configured to be connected to the expansion interface (e.g., by clipping onto the interface) such that information may be displayed to the user on a portion of the impermeable membrane while wearing the mask 100. The portion configured to display information may be transparent or semi-transparent such that the user can see the information displayed, and the user's surroundings simultaneously.

The description of certain embodiments included herein is merely exemplary in nature and is in no way intended to limit the scope of the disclosure or its applications or uses. In the included detailed description of embodiments of the present systems and methods, reference is made to the accompanying drawings which form a part hereof, and which are shown by way of illustration specific to embodiments in which the described systems and methods may be practiced. These embodiments are described in sufficient detail to enable those skilled in the art to practice presently disclosed systems and methods, and it is to be understood that other embodiments may be utilized, and that structural and logical changes may be made without departing from the spirit and scope of the disclosure. Moreover, for the purpose of clarity, detailed descriptions of certain features will not be discussed when they would be apparent to those with skill in the art so as not to obscure the description of embodiments of the disclosure. The included detailed description is therefore not to be taken in a limiting sense, and the scope of the disclosure is defined only by the appended claims.

From the foregoing it will be appreciated that, although specific embodiments of the invention have been described herein for purposes of illustration, various modifications may be made without deviating from the spirit and scope of the invention.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A protective mask comprising:
a transparent impermeable membrane;
a frame that substantially surrounds and is coupled to a perimeter of the impermeable membrane and is configured to be positioned about a face of a user;
a seal operatively coupled to the frame that seals against a face of the user and extends around a perimeter of the frame, wherein the frame and the seal are substantially impermeable to the passage of air therethrough;
an air passageway formed in the frame;

a filter element disposed to filter air passing through the air passageway, wherein the air passageway and the filter element are disposed on a bottom portion of the frame;
a sanitizing emitter positioned so as to illuminate an exterior perimeter of the filter element and acting to permeate the filter element from the exterior perimeter with a sanitizing agent operative to deactivate the particles of a damaging agent, and
a containment element that protects the user from exposure to the sanitizing agent.

2. The protective mask of claim 1, further comprising a pocket defined in the frame and configured to receive the filter element, wherein the pocket is positioned such that eyes, a nose, and a mouth of the user are not obscured by the filter element and the frame.

3. The protective mask of claim 1, wherein the seal includes a bottom extension portion that extends inward toward the interior surface of the impermeable membrane and defines an extended surface area for the seal.

4. The protective mask of claim 3, wherein the bottom extension is configured to seal against a chin of the user to maintain a seal as the user moves his mouth.

5. The protective mask of claim 2, wherein the pocket is defined on a bottom edge of the frame.

6. The protective mask of claim 2, further comprising:
a cartridge body coupled to the filter element, wherein:
the cartridge body is disposed in the air passageway; and
the cartridge body includes a lip that extends upward from a top surface of the cartridge body.

7. The protective mask of claim 6, wherein the filter element is positioned within the pocket and expands against an interior surface of the lip.

8. The protective mask of claim 7, wherein filter element is configured to substantially fill the pocket, such that substantially any air flow through the cartridge body is through the filter element.

9. The protective mask of claim 8, wherein the filter element is larger than the pocket in an uncompressed state and compressible to a second state wherein the filter element is positionable in the cartridge body via friction fit.

10. The protective mask of claim 9, wherein the cartridge body is selectively removable from the pocket.

11. A protective mask comprising:
a transparent impermeable membrane including a first portion configured to extend substantially from a forehead of a user to a chin of the user;
a frame coupled to a perimeter of the impermeable membrane; and
a seal operatively coupled to the frame that seals against a face of the user and extends around a perimeter of the frame an air passageway formed in the frame;
a filter element disposed to filter air passing through the air passageway, wherein the air passageway and the filter element are disposed on a bottom portion of the frame;
one or more sanitizing emitters positioned so as to illuminate an exterior perimeter of the filter element and acting to permeate the filter element from the exterior perimeter with a sanitizing agent operative to deactivate particles of a damaging agent, and
a containment element that protects the user from exposure to the sanitizing agent.

12. The protective mask of claim 11, wherein:

the impermeable membrane further comprises two second portions disposed on respective left and right sides of the first portion;

the impermeable membrane comprises a third portion configured to extend across the chin of the user between the two second portions; and an inflection between the first portion and the third portion is positioned below a mouth of the user.

13. The protective mask of claim 11, further comprising a cartridge receptacle coupled to the frame and configured to receive a filter assembly, the filter assembly comprising a first circuit board including the one or more sanitizing emitters.

14. The protective mask of claim 13, further comprising a first gasket including a plurality of first apertures formed therein.

15. The protective mask of claim 14, further comprising:

a second gasket including a second aperture, wherein the first circuit board, the first gasket, the filter element, and the second gasket are arranged in a stacked configuration.

16. The protective mask of claim 13, further comprising a second circuit board configured to control an aspect of the protective mask, wherein the second circuit board is disposed in within a volume defined by the frame.

17. The protective mask of claim 16, wherein the aspect of the protective mask includes at least one of the first circuit board or the one or more sanitizing emitters.

18. The protective mask of claim 11, wherein the filter element and the air passageway are configured to be positioned adjacent to or beneath the chin of the user.

\* \* \* \* \*